(12) United States Patent
Chae et al.

(10) Patent No.: US 10,781,229 B2
(45) Date of Patent: Sep. 22, 2020

(54) TRIS- OR NEOPENTYL GLYCOL-BASED AMPHIPHILES AND USES THEREOF

(71) Applicant: Industry-University Cooperation Foundation Hanyang University Erica Campus, Ansan-si (KR)

(72) Inventors: Pil Seok Chae, Ansan-si (KR); Aiman Sadaf, Ansan-si (KR)

(73) Assignee: Industry-University Cooperation Foundation Hanyang University Erica Campus, Ansan-si (KR)

( * ) Notice: Subject to any disclaimer, the term of this patent is extended or adjusted under 35 U.S.C. 154(b) by 132 days.

(21) Appl. No.: 16/061,666

(22) PCT Filed: Mar. 3, 2016

(86) PCT No.: PCT/KR2016/002154
§ 371 (c)(1),
(2) Date: Jun. 13, 2018

(87) PCT Pub. No.: WO2017/104897
PCT Pub. Date: Jun. 22, 2017

(65) Prior Publication Data
US 2019/0284221 A1     Sep. 19, 2019

(30) Foreign Application Priority Data
Dec. 14, 2015 (KR) .................. 10-2015-0177860

(51) Int. Cl.
| | | |
|---|---|---|
| C07H 15/02 | (2006.01) | |
| C07H 15/04 | (2006.01) | |
| G01N 33/68 | (2006.01) | |
| C07K 14/705 | (2006.01) | |
| C07K 1/14 | (2006.01) | |
| C07C 233/05 | (2006.01) | |
| C07H 1/06 | (2006.01) | |

(52) U.S. Cl.
CPC ........... *C07H 15/04* (2013.01); *C07C 233/05* (2013.01); *C07K 1/14* (2013.01); *C07K 14/705* (2013.01); *G01N 33/68* (2013.01); *C07H 1/06* (2013.01); *Y02P 20/55* (2015.11)

(58) Field of Classification Search
None
See application file for complete search history.

(56) References Cited

U.S. PATENT DOCUMENTS

| | | | |
|---|---|---|---|
| 6,172,262 B1 | 1/2001 | McQuade et al. | |
| 8,877,906 B2 * | 11/2014 | Gellman | C07H 15/02 530/409 |
| 2013/0001465 A1 | 1/2013 | Gellman et al. | |

FOREIGN PATENT DOCUMENTS

WO   WO 2017/104897   6/2017

OTHER PUBLICATIONS

Translation of International Search Report dated Dec. 9, 2016 From the International Searching Authority Re. Application No. PCT/KR2016/002154. (3 Pages).
Barthelemy et al. "Synthesis and Preliminary Assessments of Ethyl-Terminated Perfluoroalkyl Nonionic Surfactants Derived From Tris(Hydroxymethyl)Acrylamidomethane", Organic Letters, 1(11): 1689-1692, , Published on Web Oct. 24, 1999.
Chae et al. "Glucose-Neopentyl Glycol (GNG) Amphiphiles for Membrane Protein Study", Chemical Communications, 49(23): 2287-2289, Mar. 21, 2013.
Newstead et al. "Insights Into Outer Membrane Protein Crystallisation", Molecular Membrane Biology, 25(8): 631-638, Dec. 2008.
Newstead et al. "Rationalizing Alpha-Helical Membrane Protein Crystallization", Protein Science, 17(3): 466-472, Mar. 2008.
Sadaf et al. "A Novel Class of Glucose-Containing Amphiphiles for Membrane Proteins Study", The 115th General Meeting of the Korean Chemical Society, Apr. 15-17, 2015, p. 53, Poster ORGAN. P-736, Apr. 15, 2015.

* cited by examiner

*Primary Examiner* — Traviss C McIntosh, III

(57) ABSTRACT

The present invention relates to a TRIS- or neopentyl glycol-based amphipathic compound, a method of preparing the same, and a method of extracting, solubilizing, stabilizing, or crystallizing a membrane protein using the same. By using the TRIS- or neopentyl glycol-based compound according to the present invention, a superior membrane protein solubilization effect is exhibited, a membrane protein can be stably stored for a long time in an aqueous solution, and the structural fluidity of the membrane protein can be excellently maintained. Accordingly, the TRIS- or neopentyl glycol-based compound can be utilized in analyzing functions and structures of membrane proteins. Membrane protein structure and function analysis is currently one of the most attractive fields of research in biology and chemistry. Since more than half of the new drugs under development target membrane proteins, the compound can be applied to membrane protein structure research closely related to drug discovery.

16 Claims, 8 Drawing Sheets

TDT-C9 ($n=1$)  TDT-C11 ($n=3$)
TDT-C10 ($n=2$) TDT-C12 ($n=4$)

NDT-C9 (*n*=1)   NDT-C11 (*n*=3)
NDT-C10 (*n*=2)  NDT-C12 (*n*=4)

TRIS- OR NEOPENTYL GLYCOL-BASED AMPHIPHILES AND USES THEREOF

RELATED APPLICATIONS

This application is a National Phase of PCT Patent Application No. PCT/KR2016/002154 having International filing date of Mar. 3, 2016, which claims the benefit of priority of Korean Patent Application No. 10-2015-0177860 filed on Dec. 14, 2015. The contents of the above applications are all incorporated by reference as if fully set forth herein in their entirety.

FIELD AND BACKGROUND OF THE INVENTION

The present invention relates to a newly developed TRIS- or neopentyl glycol-based amphipathic compound and a method of extracting, solubilizing, stabilizing, crystallizing, or analyzing a membrane protein using the same.

Membrane proteins perform important functions in biological systems. These bio-macromolecules include hydrophilic and hydrophobic portions, and thus, an amphipathic molecule is necessary to extract the membrane proteins from a lipidic environment and solubilize and stabilize the same in an aqueous solution.

So as to analyze the structure of a membrane protein, a high-quality membrane protein crystal should be obtained. In order to accomplish this, the structural stability of a membrane protein in an aqueous solution should be prioritized. 100 or more existing amphipathic molecules have been used in research on membrane proteins. Thereamong, about five amphipathic molecules have been actively utilized in membrane protein structure research. The five amphipathic molecules include n-octyl-β-D-glucopyranoside (OG), n-nonyl-β-D-glucopyrano side (NG), n-decyl-β-D-maltopyranoside (DM), n-dodecyl-β-D-maltopyranoside (DDM), and lauryldimethylamine-N-oxide (LDAO) (Non-patent Documents 1 and 2). However, the structures of many membrane proteins surrounded by these molecules are easily denatured or agglomerated, thereby rapidly losing functions thereof. Accordingly, there are considerable limitations in performing research on the functions and structures of membrane proteins using these molecules. This occurs because the chemical structures of the existing molecules are simple and, accordingly, do not allow sufficient exhibition of various characteristics of the membrane proteins.

In particular, a molecule including a glucoside, as an amphipathic molecule used in structural analysis through crystallization of a membrane protein, is broadly used. However, amphipathic molecules including a glucoside have a limitation in that they do not generally excel in stabilizing membrane proteins. In particular, with regard to conventionally suggested tripod amphiphile-5 (TPA-5), as an amphipathic molecule, including three glucosides, protein extraction efficiency is very low and thus there are difficulties in commercializing the same (Patent Document 1). Therefore, there is a need for development of a novel amphipathic material having a novel structure and, accordingly, superior characteristics.

Accordingly, the present inventors developed a novel amphipathic compound which has excellent compound protein stabilization effects while having a glucoside as a hydrophilic group and, accordingly, can be used in membrane protein research, thus completing the present invention.

(Patent Document 1) U.S. Pat. No. 8,263,754 (11 Sep. 2012)
(Non-patent Document 1) S. Newstead et al., *Protein Sci.* 17 (2008) 466-472.
(Non-patent Document 2) S. Newstead et al., *Mol. Membr. Biol.* 25 (2008) 631-638.

SUMMARY OF THE INVENTION

It is an object of the present invention to provide a compound represented by Formula 1.

It is another object of the present invention to provide a composition for extracting, solubilizing, stabilizing, crystallizing or analyzing a membrane protein, the composition including the compound.

It is still another object of the present invention to provide a method of preparing the compound.

It is yet another object of the present invention to provide a method of extracting, solubilizing, stabilizing, crystallizing, or analyzing a membrane protein using the compound.

Technical Solution

In accordance with an embodiment of the present invention, there is provided a compound represented by the following Formula 1:

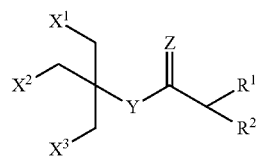

[Formula 1]

wherein $R^1$ and $R^2$ may be each independently a substituted or unsubstituted $C_3$-$C_{20}$ alkyl group, a substituted or unsubstituted $C_3$-$C_{20}$ cycloalkyl group, or a substituted or unsubstituted $C_3$-$C_{20}$ aryl group;

$X^1$, $X^2$ and $X^3$ may be each independently an oxygen-linked saccharide;

Y may be O or NH; and

Z may be absent or O.

"Saccharide," as used in the present specification, refers to a compound, a molecular size of which is relatively small, compared to other carbohydrates, and which is dissolved in water and is sweet. Saccharides are classified into monosaccharides, disaccharides, and polysaccharides depending upon the number of molecules constituting the saccharide.

The saccharide used in the embodiment may be a monosaccharide or a disaccharide. In particular, the saccharide may be glucose or maltose, more particularly glucose, but the present invention is not limited thereto.

The saccharide may function as a hydrophilic group. A compound according to an embodiment of the present invention is prepared by connecting three saccharides, as hydrophilic groups, in parallel to minimize length increase while enlarging the size of hydrophilic groups and thus reduce the size of a complex of the saccharides and a membrane protein. When the complex of the compound and the membrane protein is small, a high-quality membrane protein crystal may be obtained (G. G. Prive, *Methods* 2007, 41, 388-397). In particular, an amphipathic molecule having a small hydrophilic group, such as glucoside, may exhibit excellent effects in crystallization of a membrane protein.

In addition, $R^1$ and $R^2$ may function as a hydrophobic group. The compound according to an embodiment of the present invention includes two alkyl groups as a hydrophobic group to optimize hydrophile-lipophile balance.

The compound according to an embodiment of the present invention may include a hydrophobic group and a hydrophilic group connected by an amide or ether linkage. That is, a linker is introduced to sufficiently secure the fluidity of an alkyl chain while maintaining rigidity of the center of a molecule. In particular, the compounds according to embodiments of the present invention may have an amide linkage, in which Y is NH and Z is O, or an ether linkage, in which Y is O and Z is absent. The amide linkage may be introduced using a tris(hydroxylmethyl)aminomethane (TRIS) linker, and the ether linkage may be introduced using a neopentyl glycol linker.

In particular, $R^1$ and $R^2$ may be a $C_7$ to $C_{14}$ alkyl group; $R^1$ and $R^2$ may be the same; $X^1$ to $X^3$ may be an oxygen-linked glucose; Y may be NH; and Z may be O.

In addition, $R^1$ and $R^2$ may be a $C_7$ to $C_{14}$ alkyl group; $R^1$ and $R^2$ may be the same; $X^1$ to $X^3$ may be an oxygen-linked glucose; Y may be O; and Z may be absent.

In an example of the present invention, a compound, wherein $R^1$ and $R^2$ are a $C_9$ to $C_{12}$ alkyl group; $R^1$ and $R^2$ are the same; $X^1$ to $X^3$ are an oxygen-linked glucose; Y is NH; and Z is O compound, is designated as "TRIS-derived triglucoside (TDT)".

In another example of the present invention, a compound, wherein $R^1$ and $R^2$ are a $C_9$ to $C_{12}$ alkyl group; $R^1$ and $R^2$ are the same; $X^1$ to $X^3$ are an oxygen-linked glucose; Y is O; and Z is absent, is designated as "neopentyl glycol-derived triglucoside (NDT)".

The compound may be a compound represented by Formula 2, 3, 4, 5, 6, 7, 8, or 9 according to an example of the present invention, but the present invention is not limited thereto.

In an example of the present invention, a compound, wherein which $R^1$ and $R^2$ are a $C_9$ alkyl group; $R^1$ and $R^2$ are the same; $X^1$ to $X^3$ are an oxygen-linked glucose; Y is NH; and Z is O, is designated as "TDT-C9". Accordingly, the compound may be a compound represented by Formula 2 below:

[Formula 2]

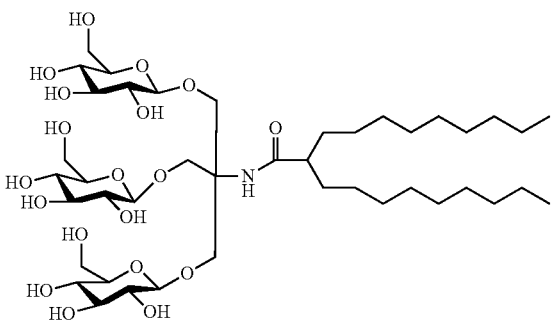

In another example of the present invention, a compound, wherein which $R^1$ and $R^2$ are a $C_{10}$ alkyl group; $R^1$ and $R^2$ are the same; $X^1$ to $X^3$ are an oxygen-linked glucose; Y is NH; and Z is O, is designated as "TDT-C10". Accordingly, the compound may be a compound represented by Formula 3 below:

[Formula 3]

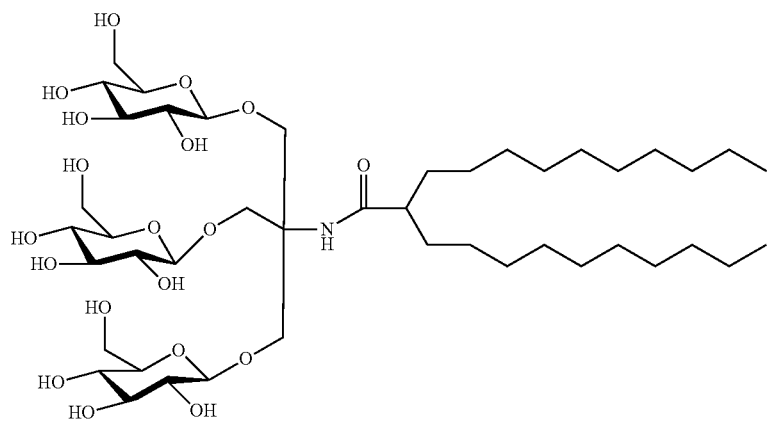

In another example of the present invention, a compound, wherein $R^1$ and $R^2$ are a $C_{11}$ alkyl group; $R^1$ and $R^2$ are the same; $X^1$ to $X^3$ are an oxygen-linked glucose; Y is NH; and Z is O, is designated as "TDT-C11". Accordingly, the compound may be a compound represented by Formula 4 below:

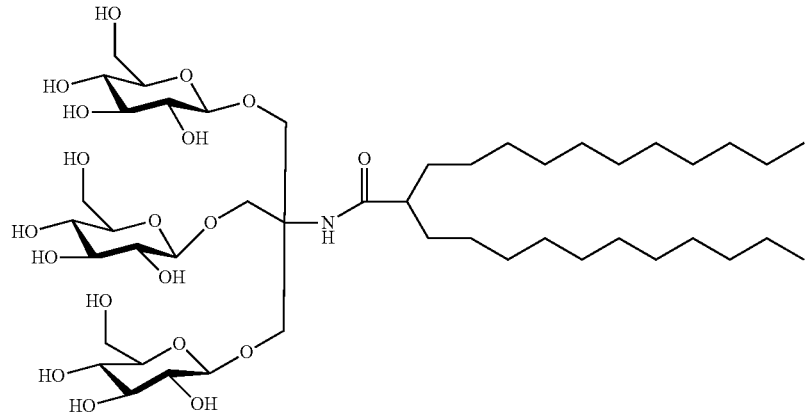

[Formula 4]

In another example of the present invention, a compound, wherein $R^1$ and $R^2$ are a $C_{12}$ alkyl group; $R^1$ and $R^2$ are the same; $X^1$ to $X^3$ are an oxygen-linked glucose; Y is NH; and Z is O, is designated as "TDT-C12". Accordingly, the compound may be a compound represented by Formula 5 below:

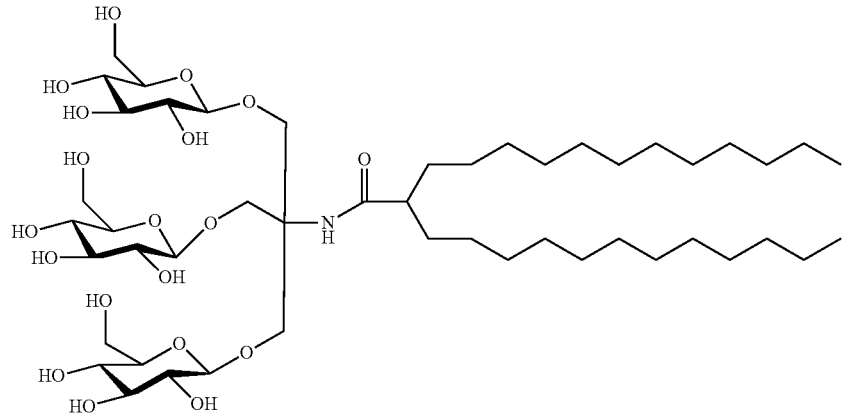

[Formula 5]

In another example of the present invention, a compound, wherein $R^1$ and $R^2$ are a $C_9$ alkyl group; $R^1$ and $R^2$ are the same; $X^1$ to $X^3$ are an oxygen-linked glucose; Y is O; and Z is absent, is designated as "NDT-C9". Accordingly, the compound may be a compound represented by Formula 6 below:

[Formula 6]

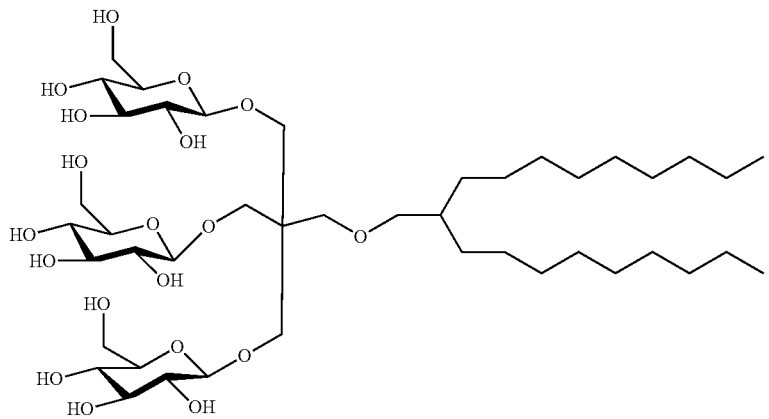

In another example of the present invention, a compound, wherein $R^1$ and $R^2$ are a $C_{10}$ alkyl group; $R^1$ and $R^2$ are the same; $X^1$ to $X^3$ are an oxygen-linked glucose; Y is O; and Z is absent, is designated as "NDT-C10". Accordingly, the compound may be a compound represented by Formula 7 below:

[Formula 7]

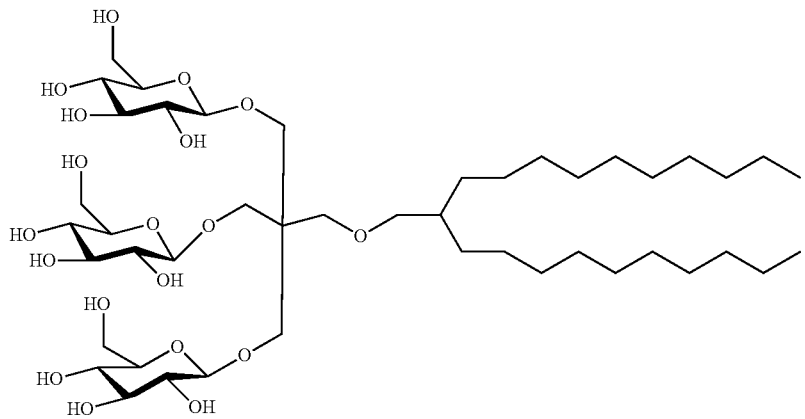

In another example of the present invention, a compound, wherein $R^1$ and $R^2$ are a $C_{11}$ alkyl group; $R^1$ and $R^2$ are the same; $X^1$ to $X^3$ are an oxygen-linked glucose; Y is O; and Z is absent, is designated as "NDT-C11". Accordingly, the compound may be a compound represented by Formula 8 below:

[Formula 8]

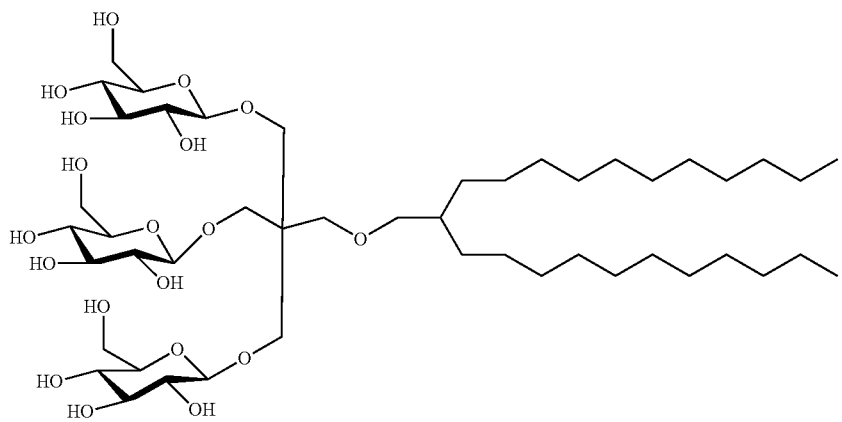

In another example of the present invention, a compound, wherein $R^1$ and $R^2$ are a $C_{12}$ alkyl group; $R^1$ and $R^2$ are the same; $X^1$ to $X^3$ are an oxygen-linked glucose; Y is O; and Z is absent, is designated as "NDT-C12". Accordingly, the compound may be a compound represented by Formula 9 below:

[Formula 9]

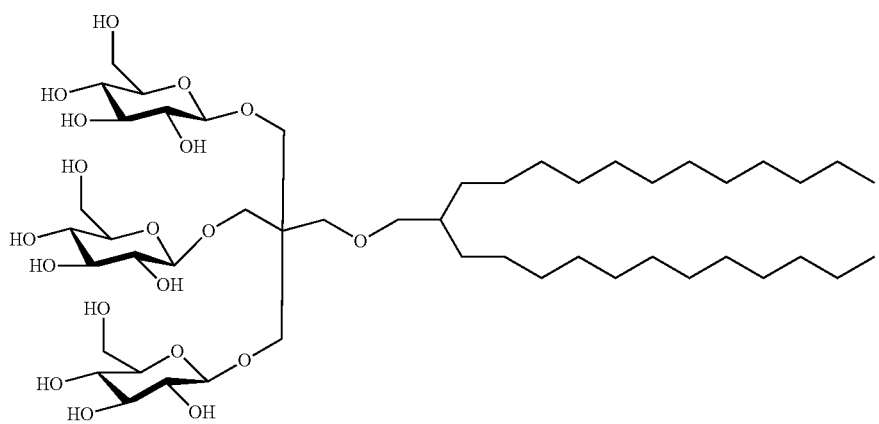

A compound according to another embodiment of the present invention may be an amphipathic molecule for extracting, solubilizing, stabilizing, crystallizing or analyzing a membrane protein, but the present invention is not limited thereto.

"Amphipathic molecule," as used in the present specification, refers to a molecule which includes hydrophobic and hydrophilic groups and thus has affinity for two types of substances, i.e., polar and nonpolar solvents. Phospholipid molecules present in a surfactant or a cellular membrane are amphipathic, i.e., have hydrophilic groups at one end thereof and hydrophobic groups at the other end, and form micelles or liposomes in an aqueous solution. Since the hydrophilic groups have polarity and nonpolar groups coexist with the hydrophilic groups, the amphipathic molecules tend not to be readily soluble in water. However, when the concentration of the molecules is equal to or greater than a critical micellar concentration (CMC), the hydrophobic groups are gathered in the interiors of the molecules by hydrophobic interaction and thus micelles, at surfaces of which hydrophilic groups gather, are generated, whereby solubility of the molecules in water increases.

A method of measuring the CMC is not specifically limited and may be a method which is generally known in the art. For example, the CMC may be measured according to a fluorescence staining method using diphenylhexatriene (DPH).

The compound according to an embodiment of the present invention may have a critical micellar concentration (CMC) of 0.1 μM to 500 μM, particularly 0.1 μM to 100 μM, more particularly, 0.1 μM to 80 μM, even more particularly, 0.5 μM to 80 μM, in an aqueous solution. For example, the CMC may be 1 μM to 50 μM, but the present invention is not limited thereto.

Compared to DDM, which is conventionally and mainly used in research on membrane proteins, having a critical micellar concentration of 170 μM, TDTs or NDTs of the present embodiment have a smaller CMC value. Accordingly, since even a small amount of TDTs or NDTs easily forms micelles, membrane proteins may be efficiently studied and analyzed using a small amount of TDTs or NDTs. Therefore, TDTs and NDTs are more advantageous than DDM.

In addition, another embodiment of the present invention provides a composition for extracting, solubilizing, stabilizing, crystallizing or analyzing a membrane protein, the composition including the compound.

The composition may be a micelle, liposome, emulsion, or nanoparticle formulation, but the present invention is not limited thereto.

The radius of the micelle may be 2.0 nm to 60.0 nm, particularly 3.0 nm to 55.0 nm. More particularly, the radius of a micelle formed of TDTs according to examples of the present invention may be 2.0 nm to 60.0 nm. For example, the radius may be 3.0 to 55.0 nm. Even more particularly, the radius of a micelle formed of NDTs according to other examples of the present invention may be 2.0 nm to 4.5 nm. For example, the radius may be 3.0 nm to 4.0 nm, but the present invention is not limited thereto.

A method of measuring the radius of a micelle is not specifically limited and may be any method generally known in the art. For example, the radius may be measured by a dynamic light scattering (DLS) experiment.

While the sizes of micelles formed of NDTs are almost similar to those of DDM, TDTs form micelles with varying sizes. Accordingly, it can be confirmed that a small chemical structure difference between TDTs and NDTs (i.e., structural difference between amide and ether) considerably affects a self-aggregation pattern in an aqueous solution.

The micelle, the liposome, the emulsion or the nanoparticle may include a membrane protein in the interior thereof. That is, the micelle, liposome, emulsion or nanoparticle may extract and envelop a membrane protein present inside a cellular membrane. Accordingly, it is possible to extract, solubilize, stabilize, crystallize or analyze a membrane protein using the micelle.

The composition may additionally include a buffer, etc. which helps to extract, solubilize, stabilize or analyze a membrane protein.

In addition, another embodiment of the present invention provides a method of preparing a compound represented by the following Formula 1, the method including steps 1) to 5) below:

1) generating dialkylated dimethylmalonate by adding alkyl iodide to dimethylmalonate;
2) generating dialkylated monoester by allowing demethoxy carbonylation of a product generated by step 1);
3) introducing an amide linker by adding tris(hydroxymethyl)aminomethane to a product generated by step 2);
4) introducing a saccharide, to which a protective group is attached, by allowing glycosylation of a product generated by step 3); and
5) removing an O-benzoyl group by allowing deprotection of a product generated by step 4):

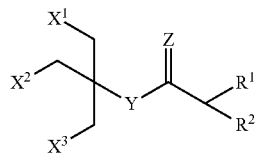

[Formula 1]

wherein $R^1$ and $R^2$ may be a $C_7$ to $C_{14}$ alkyl group; $R^1$ and $R^2$ may be the same; $X^1$ to $X^3$ may be an oxygen-linked glucose; Y may be NH; and Z may be O.

The preparation method according to the embodiment may be a method of preparing TDTs according to an example of the present invention, but the present invention is not limited thereto.

In the embodiment, a compound may be synthesized using a simple method constituted of five synthesis steps using dimethylmalonate, as a starting material. As such, since a compound may be easily synthesized according to the preparation method of the present invention, a compound used in performing research into membrane proteins may be mass-produced.

In addition, another embodiment of the present invention provides a method of preparing a compound represented by the following Formula 1, the method including steps 1) to 5) below:

1) generating dialkylated dimethylmalonate by adding alkyl iodide to dimethylmalonate;
2) generating dialkylated mono-ol by allowing dialkylated ester reduction of a product generated by step 1);
3) generating dialkylated tri-ol, into which an ether linker is introduced, by adding 4-(bromomethyl)-1-methyl-2,6,7-trioxabicyclo[2.2.2]-octane to a product generated by step 2);
4) introducing a saccharide, to which a protective group is attached, by allowing glycosylation of a product generated by step 3); and
5) removing an O-benzoyl group by allowing deprotection of a product generated by step 4):

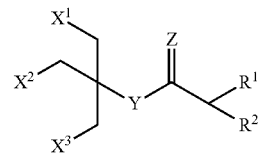

[Formula 1]

wherein $R^1$ and $R^2$ may be a $C_7$ to $C_{14}$ alkyl group; $R^1$ and $R^2$ may be the same; $X^1$ to $X^3$ may be an oxygen-linked glucose; Y may be O; and Z may be absent.

The preparation method according to the embodiment may be a method of preparing NDTs according to another example of the present invention, but the present invention is not limited thereto.

In the embodiment, a compound may be synthesized in a simple method constituted of five synthesis steps using dimethylmalonate, as a starting material. As such, since a compound may be easily synthesized according to the preparation method of the present invention, a compound used in performing research into a membrane protein may be mass-produced.

In an example of the present invention, the following steps are carried out according to a synthesis scheme illustrated in FIG. 1 to prepare TDT-C9 to TDT-C12:

1) generating dialkylated dimethylmalonate (Compound A) by adding NaH and alkyl iodide to a DMSO solution in which dimethylmalonate is dissolved;
2) generating dialkylated methyl ester (Compound B) by adding LiCl and $H_2O$ to Compound A dissolved in DMSO and performing demethoxy carbonylation through heating to 160° C.;
3) generating Compound C, to which an amide linker is introduced, by adding TRIS(tris(hydroxymethyl)aminomethane) and NaOMe to Compound B dissolved in DMSO and reacting the same at 50° C.;
4) generating Compound D, into which glucose including a protective group connected thereto is introduced, by adding AgOTf, 2,4,6-collidine and $CH_2Cl_2$ to Compound C and reacting the same at −45° C., followed by additionally adding perbenzoylated glucosylbromide thereto to allow glycosylation; and 5) generating Compound E, from which an O-benzoyl group is removed, by adding NaOMe and MeOH to Compound D to allow deprotection.

In an example of the present invention, the following steps were carried out according to a synthesis scheme illustrated in FIG. 3 to prepare NDT-C9 to NDT-C12:

1) generating dialkylated dimethylmalonate (Compound A) by adding NaH and alkyl iodide to a DMSO solution in which dimethylmalonate is dissolved;

2) generating dialkylated mono-ol (Compound B) by adding LiCl and $H_2O$ to Compound A dissolved in DMSO and heating the same at 160° C. to allow demethoxycarbonylation, followed by obtaining an intermediate product through an extraction process, and adding $LiAlH_4$ and THF to the intermediate product to allow reduction of dialkylated ester;

3) generating dialkylated tri-ol (Compound C), into which an ether linker is introduced, by adding 4-(bromomethyl)-1-methyl-2,6,7-trioxabicyclo[2.2.2]-octane and NaH, which are dissolved in THF, to Compound B dissolved in DMF and allowing reaction thereof through heating at 100° C., followed by obtaining an intermediate product through an extraction process, dissolving the obtained intermediate product in DCM and MeOH, and sequentially introducing HCl and NaOH to the dissolved product;

4) generating Compound D, into which glucose including a protective group connected thereto is introduced, by adding AgOTf, 2,4,6-collidine and $CH_2Cl_2$ to Compound C and reacting the same at −45° C., followed by additionally adding perbenzoylated glucosylbromide thereto to allow glycosylation; and 5) generating Compound E, from which an O-benzoyl group is removed, by adding NaOMe and MeOH to Compound D to allow deprotection.

In addition, another embodiment of the present invention provides a method of extracting, solubilizing, stabilizing, crystallizing, or analyzing a membrane protein. In particular, the present invention provides a method of extracting, solubilizing, stabilizing, crystallizing, or analyzing a membrane protein, the method including treating a membrane protein in an aqueous solution with a compound represented by the following Formula 1:

[Formula 1]

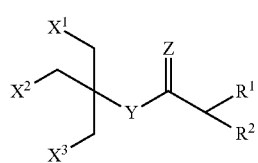

wherein $R^1$ and $R^2$ may be each independently a substituted or unsubstituted $C_3$-$C_{20}$ alkyl group, a substituted or unsubstituted $C_3$-$C_{20}$ cycloalkyl group, or a substituted or unsubstituted $C_3$-$C_{20}$ aryl group;

$X^1$, $X^2$ and $X^3$ may be each independently an oxygen-linked saccharide;

Y may be O or NH; and

Z may be absent or O.

In particular, $R^1$ and $R^2$ may be a $C_7$ to $C_{14}$ alkyl group; $R^1$ and $R^2$ may be the same; $X^1$ to $X^3$ may be an oxygen-linked glucose; Y may be NH; and Z may be O, although the present invention is not limited thereto.

In addition, $R^1$ and $R^2$ may be a $C_7$ to $C_{14}$ alkyl group; $R^1$ and $R^2$ may be the same; $X^1$ to $X^3$ may be an oxygen-linked glucose; Y may be O; and Z may be absent, although the present invention is not limited thereto.

The compound may be a compound represented by Formula 2, 3, 4, 5, 6, 7, 8, or 9 according to an example of the present invention, but the present invention is not limited thereto.

"Membrane protein," as used in the present specification, is a generic term for proteins or glycoproteins in a lipid bilayer of a cellular membrane. Membrane proteins are present in various states, i.e., membrane proteins may cross entire layers of a cellular membrane, be located on a surface layer, or adhere to a cellular membrane. Examples of membrane proteins include enzymes, peptide hormones, receptors such as local hormones, receptor carriers such as saccharides, ion channels, cellular membrane antigens, etc., but the present invention is not limited thereto.

The membrane protein may be any protein or glycoprotein which ingresses into a lipid bilayer of a cellular membrane. In particular, the membrane protein may be a uric acid-xanthine/H+ symporter (UapA), a melibiose permease (MelB), a leucine transporter (LeuT), a G-protein coupled receptor (GPCR), or a combination of two or more thereof, but the present invention is not limited thereto.

"Extraction of a membrane protein," as used in the present specification, refers to extracting a membrane protein from a cellular membrane.

"Solubilization of a membrane protein," as used in the present specification, refers to dissolving a membrane protein, which does not dissolve in an aqueous solution, in a micelle.

"Stabilization of a membrane protein," as used in the present specification, refers to stably preserving a tertiary or quaternary structure of a membrane protein such that the structure and function of the membrane protein are not changed.

"Crystallization of a membrane protein," as used in the present specification, refers to forming a crystal of a membrane protein in a solution.

"Analysis of a membrane protein," as used in the present specification, refers to analyzing the structure or function of a membrane protein. In the embodiment, the membrane protein analysis may be carried out according to a publicly known method. For example, the membrane protein analysis may be carried out by means of electron microscopy, but the present invention is not limited thereto.

Amphipathic molecules used in research into a membrane protein are greatly affected by small changes in chemical structure. TDTs and NDTs according to the present invention have similar structures wherein a triglucoside group is connected to two flexible alkyl chains via an inflexible linker (TRIS or NPG). The two amphipathic molecules have a structural difference with regard to a functional group of a linker. While TDTs have an amide linkage, NDTs have an ether linkage. Despite such a small difference in the chemical structures thereof, the two amphipathic molecules exhibited greatly different efficiencies in all tested membrane proteins (UapA, MelB, and LeuT). The efficiency of NDTs (particularly NDT-C11) was remarkably superior to that of TDTs. The sizes of micelles formed of the two amphipathic molecules were also confirmed as being greatly different. Micelles formed of TDTs were larger than micelles formed of NDTs, an alkyl chain length of which was the same as that of TDTs. A rigidity difference between the amide linkage and the ether linkage is considered to be related to such a micelle size difference and membrane protein stabilization efficiencies. In particular, since an alkyl chain connected by an ether linkage has high flexibility, micelles are more easily formed, compared to a compound having an amide linkage. The flexible linker of NDTs also serves to reduce the sizes of self-assemblies of the NDTs, which have a relatively small CMC value, compared to TDTs. The flexibility of the ether linkage allows density increase of alkyl chains of amphipathic molecules surrounding a membrane protein, thereby being strongly packed on a surface of the membrane protein and, accordingly, enhancing stability of a target protein.

In addition, a small glucoside group of the amphipathic molecule of the present invention tends to form a small protein-detergent complex (PDC). The small PDC provides a wide hydrophilic protein surface, thus being advantageous in crystallizing a membrane protein. Crystal formation is facilitated by interaction between a hydrophilic portion of a membrane protein and an amphipathic molecule. Advantages of a small hydrophilic group of an amphipathic molecule are related to the reason why existing amphipathic glucoside molecules (OG and NG) are broadly utilized in crystallizing membrane proteins. On the other hand, an amphipathic molecule having a small hydrophilic group such as glucose is disadvantageous in stabilizing a membrane protein, compared to an amphipathic molecule having relatively large maltoside as a hydrophilic group. Accordingly, up to now, an amphipathic glucoside molecule having superior membrane protein stabilization effects to DDM has not been developed. However, it was confirmed that TDTs and NDTs according to the present invention had superior membrane protein stabilization effects to DDM despite the inclusion of glucose as a hydrophilic group, and thus, they are ideally suited to stabilization of a membrane protein as well as crystallization of a membrane protein.

In addition, when NDT-C11 according to an example of the present invention was compared to maltose-neopentyl glycol (MNG)-3 amphiphiles, one of the most promising novel amphipathic molecules, NDT-C11 was similar to MNG-3 in providing a degree of high membrane protein stabilization, but was superior to MNG-3 in providing structural flexibility essential for protein functions. Such results show that NDT-C11 can be used as an optimal novel compound in biophysical research in which proteins having a stable structure and maintaining functions thereof are required.

By using a TRIS- or neopentyl glycol-based compound according to embodiments of the present invention, a membrane protein can be stably stored for a long time in an aqueous solution and the structural fluidity of the membrane protein can be excellently maintained, compared to existing compounds. Accordingly, the TRIS- or neopentyl glycol-based compound can be utilized in analyzing functions and structures of membrane proteins.

Membrane protein structure and function analysis is currently one of the most attractive fields of research in biology and chemistry. Since more than half of the new drugs under development target membrane proteins, the compound can be applied to protein structure research closely related to drug discovery.

In particular, since the compounds according to embodiments of the present invention have a small hydrophilic group, they have excellent effects in crystallizing a membrane protein. In addition, the compounds exhibit superior membrane protein stability to existing compounds, without slight decrease in membrane protein stability occurring due to use of a small hydrophilic group.

In addition, since the compounds according to embodiments of the present invention can be synthesized using a simple method from easily obtainable starting materials, the compounds can be mass-produced to perform research into membrane proteins.

DESCRIPTION OF SPECIFIC EMBODIMENTS OF THE INVENTION

Hereinafter, the present invention will be described in more detail with reference to the following examples. However, the following examples are provided to exemplify contents of the present invention and the scope of the present invention is not limited to the following examples. It should be understood that examples which can be easily deduced from detailed descriptions and the following examples of the present invention by one of ordinary skill in the art are within the scope of the present invention.

<Example 1> Method of Synthesizing TRIS-Derived Triglucosides (TDTs)

Figure 1:
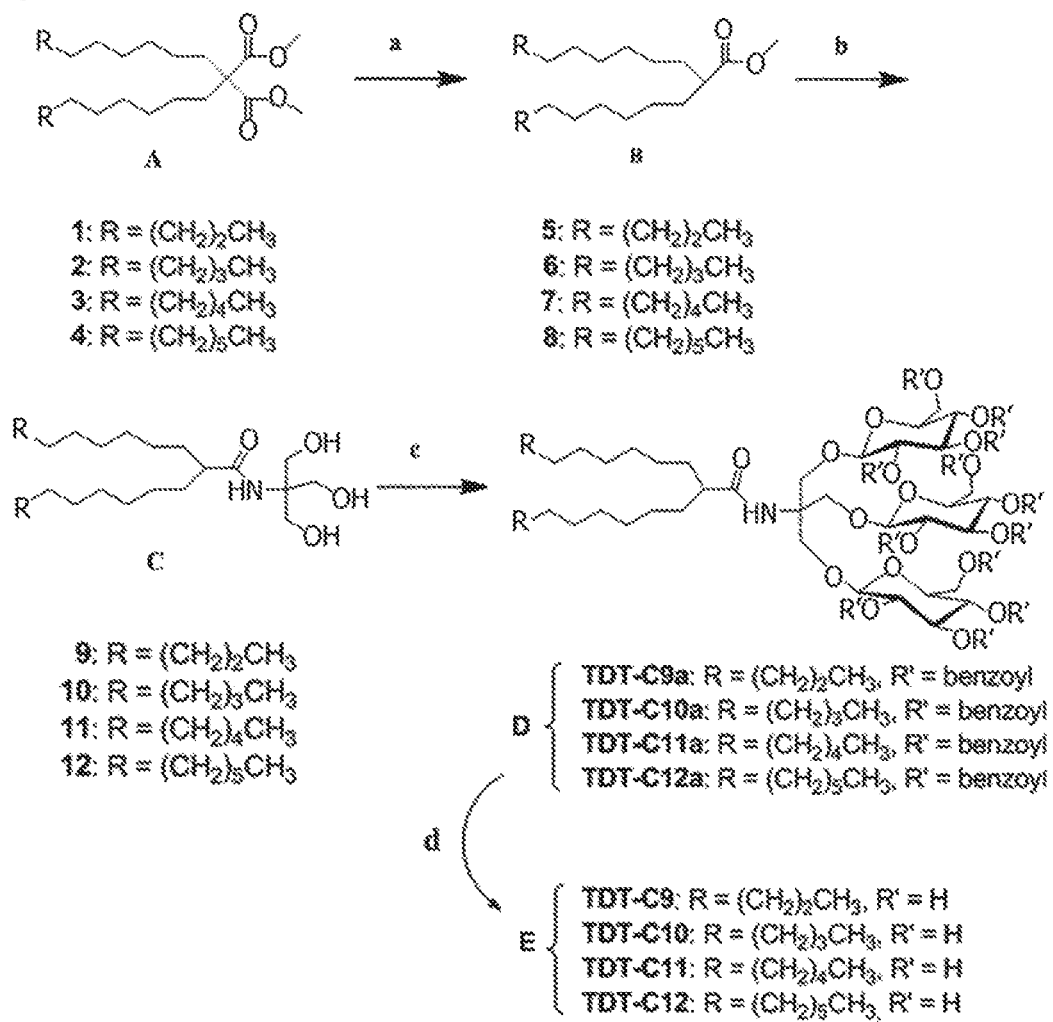
FIG. 1 illustrates a synthesis scheme of TDTs according to Example 1 of the present invention.
Figure 2:
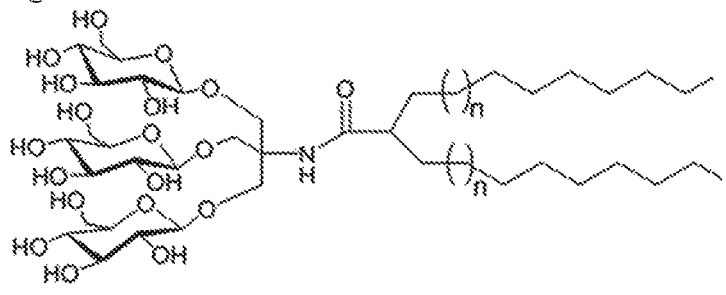
FIG. 2 illustrates chemical structures of TDTs according to the examples of the present invention.

A synthesis scheme of TDTs is illustrated in FIG. 1. According to synthesis methods of <1-1> to <1-5> below, four tris(hydroxylmethyl)aminomethane(TRIS)-derived triglucosides (TDTs) were synthesized, as illustrated in FIG. 2.

<1-1> General Synthesis Procedure of Dialkylated Dimethylmalonate (Synthesis of Compound A)

Dimethylmalonate (1.0 equiv.) was added dropwise to a DMSO solution in which NaH (3.0 equiv.) was dissolved and which was kept cold using an ice bath. A resultant mixture was stirred until gas generation was terminated. Alkyl iodide (2.5 equiv.) was slowly added to the resultant solution. An obtained mixture was stirred for three hours at room temperature. The reaction was terminated by adding a cold 10% $NH_4Cl$ solution to the mixture. An obtained solution was washed with ethyl acetate twice. An organic ethyl acetate layer was collected and then washed with brine, followed by drying with anhydrous $Na_2SO_4$. A resultant product was concentrated with an organic solvent to obtain a residual oil. The residual oil was purified by column chromatography (EtOAc/hexane). As a result, a desired product, i.e., dialkylated dimethylmalonate (Compound A) was obtained as a colorless oil.

<1-2> General Procedure for Demethoxy Carbonylation Under Krapcho Decarboxylation Condition (Step a; A→B)

LiCl (2.2 equiv.) and distilled water (1.1 equiv.) were added to a DMSO solution in which Compound A was dissolved. A resultant mixture was stirred for several minutes and then heated at 160° C. for 12 hours. Brine was added to the reacted mixture, followed by extracting with EtOAc twice. An organic layer was collected and then washed with brine, followed by drying with anhydrous $Na_2SO_4$. A reacted mixture was concentrated by means of a rotary evaporator to obtain a dark residual oil. After purifying by column chromatography, a desired dialkylated monoester (Compound B) was obtained as a colorless oil.

<1-3> General Procedure for Tris Coupling with Dialkylated Methyl Ester (Step b; B→C)

Tris(hydroxymethyl)aminomethane (1.5 equiv.) and NaOMe (2.0 equiv.) were added to a mixture of dialkylated methyl ester (Compound B) (1.0 equiv.) dissolved in DMSO under a nitrogen atmosphere. A resultant solution was stirred at 50° C. for six hours. A reacted mixture was diluted with water and then extracted with ethyl acetate. An organic layer was washed with brine and dried with anhydrous $Na_2SO_4$. A resultant ethyl acetate solution was concentrated and then a residue was purified by flash column chromatography (EtOAc/hexane), thereby a desired product, i.e., Compound C was obtained as a white solid.

<1-4> General Procedure for Glycosylation (Step c; C→D)

Under a nitrogen atmosphere, a mixture of Compound C (1.0 equiv.), AgOTf (3.6 equiv.), and 2,4,6-collidine (1.0 equiv.) dissolved in anhydrous $CH_2Cl_2$ was stirred at −45° C. To this resultant suspension, a solution including perbenzoylated glucosylbromide (3.6 equiv.) dissolved in $CH_2Cl_2$ was slowly added. Continuous stirring was performed at 45° C. for 30 minutes. Subsequently, the temperature of the reacted mixture was lowered to 0° C., followed by re-stirring at the same temperature for 1.5 hours. After completing the reaction (reaction completion was determined by TLC), pyridine was added to the reacted mixture, followed by diluting with $CH_2Cl_2$ and then filtering with Celite. A filtrate was continuously washed with an aqueous 1 M $Na_2S_2O_3$ solution, an aqueous 0.1 M HCl solution, and brine. An organic layer was dried with anhydrous $Na_2SO_4$ and the solvent was removed therefrom by means of a rotary evaporator. A residue was purified by silica gel column chromatography (EtOAc/hexane) to obtain a desired product, i.e., Compound D, as a glassy solid.

<1-5> General Procedure for De-O-Benzoylation Under Zemplén Conditions (Step d; DE)

An O-benzoylated (benzoylated) compound (Compound D) was dissolved in MeOH, followed by treating with 0.5 M NaOMe, as a methanolic solution, in a necessary amount such that a final concentration of NaOMe became 0.05 M. A reacted mixture was stirred at room temperature for six hours and then neutralized with Amberlite IR-120 (H+ form) resin. The resin was removed from the reacted mixture by filtration and washed with MeOH, and the solvent was removed from the reacted mixture under vacuum. A residue was purified by silica gel column chromatography (MeOH/$CH_2Cl_2$) to obtain a desired product, i.e., Compound E, as a white solid. The obtained Compound E was designated as TRIS-derived triglucosides (TDTs).

<Preparation Example 1> Synthesis of TDT-C9

<1-1> Synthesis of Dimethyl 2-Nonylmalonate (Compound 1)

According to the dialkylated dimethylmalonate synthesis method of Example 1-1, dimethyl 2-nonylmalonate (Compound 1) was synthesized in a yield of 91% using nonyl iodide as alkyl iodide. $^1$H NMR (400 MHz, $CDCl_3$): δ 3.70 (s, 6H), 1.88-1.83 (m, 4H), 1.34-1.05 (m, 28H), 0.87 (t, J=7.2 Hz, 6H); $^{13}$C NMR (100 MHz, $CDCl_3$): δ 172.34, 57.56, 52.05, 31.83, 29.75, 29.43, 29.27, 29.23, 23.93, 22.61, 14.00.

<1-2> Synthesis of Methyl 2-Nonylundecanoate (Compound 5)

Demethoxy carbonylation was carried out according to the method of Example 1-2 and methyl 2-nonylundecanoate (Compound 5) was synthesized in a yield of 80%. $^1$H NMR (400 MHz, $CDCl_3$): δ 3.66 (s, 3H), 2.32-2.23 (m, 1H), 1.67-1.40 (m, 4H) 1.34-1.25 (m, 28H), 0.87 (t, J=7.2 Hz, 6H); $^{13}$C NMR (100 MHz, CDCl$_3$): δ 169.81, 61.50, 52.32, 33.10, 29.80, 29.73, 29.54, 29.42, 28.91, 27.51, 22.93, 14.30.

<1-3> Synthesis of N-(1,3-dihydroxy-2-(hydroxymethyl)propane-2-yl)-2-nonylundecanamide (Compound 9)

Tris coupling was carried out according to the method of Example 1-3 and N-(1,3-dihydroxy-2-(hydroxymethyl)propane-2-yl)-2-nonylundecanamide (Compound 9) was synthesized in a yield of 74%. $^1$H NMR (400 MHz, CDCl$_3$): δ 6.48 (s, 1H), 4.64 (br s, 3H), 3.60 (s, 6H), 2.10-2.03 (m, 1H), 1.65-1.33 (m, 4H), 1.38-1.20 (m, 28H), 0.88 (t, J=6.8 Hz, 6H); $^{13}$C NMR (100 MHz, CDCl$_3$): δ 178.44, 131.03, 128.96, 62.51, 60.25, 48.17, 33.05, 32.02, 29.76, 29.70, 29.62, 29.42, 27.66, 22.81, 14.24.

<1-4> Synthesis of TDT-C9a

Glycosylation was carried out according to the method of Example 1-4 and TDT-C9a was synthesized in a yield of 75%. $^1$H NMR (400 MHz, CDCl$_3$): δ 8.10-7.80 (m, 18H), 7.60-7.10 (m, 42H), 5.75 (s, 1H), 5.63 (t, J=9.6 Hz, 3H), 5.51 (t, J=9.6 Hz, 3H), 5.38 (t, J=8.0 Hz, 3H), 4.45-4.32 (m, 6H), 4.02 (d, J=8.0 Hz, 3H), 3.78 (d, J=9.6 Hz, 3H), 3.4-3.3 (m, 3H), 3.21-3.05 (m, 6H), 1.80-1.65 (m, 1H), 1.45-1.10 (m, 32H), 0.86 (t, J=6.8 Hz, 6H); $^{13}$C NMR (100 MHz, CDCl$_3$): δ 176.42, 166.08, 165.71, 165.07, 164.64, 133.77, 133.49, 133.32, 133.31, 129.95, 129.84, 129.74, 129.70, 129.63, 129.58, 129.42, 129.09, 128.86, 128.80, 128.35, 101.47, 72.63, 71.95, 69.54, 68.19, 62.95, 59.36, 32.85, 32.03, 31.98, 29.96, 29.75, 29.46, 27.56, 27.35, 22.75, 14.21.

<1-5> Synthesis of TDT-C9

Deprotection was carried out according to the method of Example 1-5 and TDT-C9 having two C$_9$ alkyl groups was synthesized in a yield of 90%. $^1$H NMR (400 MHz, CD$_3$OD): δ 4.50-4.31 (m, 6H), 3.89-3.85 (m, 6H), 3.67-3.63 (m, 3H), 3.37-3.17 (m, 12H), 2.2-2.1 (m, 1H), 1.38-1.21 (m, 32H), 0.80 (t, J=6.8 Hz, 6H); $^{13}$C NMR (100 MHz, CD$_3$OD): δ 179.57, 104.87, 78.13, 78.11, 75.21, 71.85, 69.46, 62.94, 61.22, 34.40, 34.32, 33.25, 33.23, 31.24, 31.01, 30.92, 30.84, 30.62, 28.72, 28.59, 23.88, 14.59. HRMS (EI): calcd. for C$_{42}$H$_{79}$NO$_{19}$[M+Na]$^+$ 924.5144, found 924.5143.

<Preparation Example 2> Synthesis of TDT-C10

<2-1> Synthesis of Dimethyl 2-Decylmalonate (Compound 2)

According to the dialkylated dimethylmalonate synthesis method of Example 1-1, dimethyl 2-decylmalonate (Compound 2) was synthesized in a yield of 91% using decyl iodide as alkyl iodide. $^1$H NMR (400 MHz, CDCl$_3$): δ 3.70 (s, 6H), 1.88-1.83 (m, 4H), 1.34-1.25 (m, 32H), 0.87 (t, J=7.2 Hz, 6H); $^{13}$C NMR (100 MHz, CDCl$_3$): δ 172.55, 57.76, 52.25, 32.50, 32.03, 29.93, 29.71, 29.66, 29.45, 24.11, 23.66, 22.80, 14.20.

<2-2> Synthesis of Methyl 2-Decylundecanoate (Compound 6)

Demethoxy carbonylation was carried out according to the method of Example 1-2 and methyl 2-decylundecanoate (Compound 6) was synthesized in a yield of 82%. $^1$H NMR (400 MHz, CDCl$_3$): δ 3.66 (s, 3H), 2.32-2.23 (m, 1H), 1.67-1.40 (m, 4H), 1.34-1.25 (m, 32H), 0.87 (t, J=7.2 Hz, 6H); $^{13}$C NMR (100 MHz, CDCl$_3$): δ 169.81, 61.53, 52.30, 32.10, 29.80, 29.70, 29.51, 29.41, 28.93, 27.53, 22.94, 14.31.

<2-3> Synthesis of N-(1,3-dihydroxy-2-(hydroxymethyl)propane-2-yl)-2-decylundecanamide (Compound 10)

Tris coupling was carried out according to the methods of Example 1-3 and N-(1,3-dihydroxy-2-(hydroxymethyl)propane-2-yl)-2-decylundecanamide (Compound 10) was synthesized in a yield of 72%. $^1$H NMR (400 MHz, CDCl$_3$): δ 6.49 (s, 1H), 5.20-5.1 (br s, 3H), 3.57 (s, 6H), 2.10-2.01 (m, 1H), 1.65-1.39 (m, 4H), 1.38-1.20 (m, 32H), 0.88 (t, J=6.8 Hz, 6H); $^{13}$C NMR (100 MHz, CDCl$_3$): δ 178.30, 131.03, 62.35, 60.12, 48.03, 33.09, 31.90, 29.62, 29.58, 29.48, 29.33, 27.52, 22.68, 14.11.

<2-4> Synthesis of TDT-C10a

Glycosylation was carried out according to the method of Example 1-4 and TDT-C10a was synthesized in a yield of 80%. $^1$H NMR (400 MHz, CDCl$_3$): δ 8.10-7.80 (m, 18H), 7.60-7.10 (m, 42H), 5.75 (s, 1H), 5.63 (t, J=9.6 Hz, 3H), 5.51 (t, J=9.6 Hz, 3H), 5.38 (t, J=8.0 Hz, 3H), 4.45-4.32 (m, 6H), 4.02 (d, J=8.0 Hz, 3H), 3.78 (d, J=9.6 Hz, 3H), 3.4-3.3 (m, 3H), 3.21-3.05 (m, 6H), 1.80-1.65 (m, 1H), 1.45-1.10 (m, 36H), 0.86 (t, J=6.8 Hz, 6H); $^{13}$C NMR (100 MHz, CDCl$_3$): δ 176.52, 166.18, 165.80, 165.15, 164.72, 133.82, 133.57, 133.38, 133.26, 130.04, 129.93, 129.90, 129.81, 129.73, 129.67, 129.54, 129.12, 128.98, 128.92, 128.56, 128.44, 101.52, 72.70, 72.01, 69.62, 68.24, 63.03, 59.40, 32.89, 32.07, 30.01, 29.85, 29.60, 29.55, 27.64, 27.43, 22.84, 14.26.

<2-5> Synthesis of TDT-C10

Deprotection was carried out according to the method of Example 1-5 and TDT-C10 having two Cm alkyl groups were synthesized in a yield of 95%. $^1$H NMR (400 MHz, CD$_3$OD): δ 4.50-4.31 (m, 6H), 3.89-3.85 (m, 6H), 3.67-3.63 (m, 3H), 3.37-3.17 (m, 12H), 2.2-2.1 (m, 1H), 1.38-1.21 (m, 36H), 0.80 (t, J=6.8 Hz, 6H); $^{13}$C NMR (100 MHz, CD$_3$OD): δ 179.67, 104.87, 78.13, 75.22, 71.86, 69.50, 62.95, 61.32, 34.39, 34.32, 33.24, 31.24, 31.07, 30.98, 30.92, 30.86, 30.84, 30.66, 28.73, 28.60, 23.89, 14.62. HRMS (EI): calcd. for C$_{44}$H$_{83}$NO$_{19}$[M+Na]$^+$ 952.5457, found 952.5454.

<Preparation Example 3> Synthesis of TDT-C11

<3-1> Synthesis of Dimethyl 2-Undecylmalonate (Compound 3)

According to the dialkylated dimethylmalonate synthesis method of Example 1-1, dimethyl 2-undecylmalonate (Compound 3) was synthesized in a yield of 86% using undecyl iodide as alkyl iodide. $^1$H NMR (400 MHz, CDCl$_3$): δ 3.70 (s, 6H), 1.88-1.83 (m, 4H), 1.30-1.24 (m, 36H), 0.87 (t, J=7.2 Hz, 6H); $^{13}$C NMR (100 MHz, CDCl$_3$): δ 172.44, 57.71, 52.15, 51.21, 45.78, 32.63, 32.49, 32.03, 29.91, 29.74, 29.64, 29.47, 29.43, 27.58, 24.09, 22.79, 14.16.

<3-2> Synthesis of Methyl 2-Undecylundecanoate (Compound 7)

Demethoxy carbonylation was carried out according to the method of Example 1-2 and methyl 2-undecylundecanoate (Compound 7) was synthesized in a yield of 78%. $^1$H NMR (400 MHz, CDCl$_3$): δ 3.66 (s, 3H), 2.32-2.23 (m, 1H), 1.67-1.40 (m, 4H), 1.30-1.24 (m, 40H), 0.87 (t, J=7.2 Hz, 6H); $^{13}$C NMR (100 MHz, CDCl$_3$): δ 169.81, 61.54, 52.32, 33.10, 29.81, 29.72, 29.64, 29.42, 28.92, 27.53, 22.91, 14.32.

<3-3> Synthesis of N-(1,3-dihydroxy-2-(hydroxymethyl)propane-2-yl)-2-undecylundecanamide (Compound 11)

Tris coupling was carried out according to the method of Example 1-3 and N-(1,3-dihydroxy-2-(hydroxymethyl)propane-2-yl)-2-undecylundecanamide (Compound 11) was synthesized in a yield of 70%. $^1$H NMR (400 MHz, CDCl$_3$): δ 6.51 (s, 1H), 5.63 (br s, 3H), 3.54 (s, 6H), 2.12-2.05 (m, 1H), 1.55-1.31 (m, 4H), 1.38-1.20 (m, 36H), 0.88 (t, J=6.8 Hz, 6H); $^{13}$C NMR (100 MHz, CDCl$_3$): δ 178.30, 131.03, 62.45, 60.12, 48.33, 33.09, 31.90, 29.65, 29.58, 29.48, 29.33, 28.43, 27.52, 22.68, 14.09.

<3-4> Synthesis of TDT-C11

Glycosylation was carried out according to the method of Example 1-4 and TDT-C11a was synthesized in a yield of 65%. $^1$H NMR (400 MHz, CDCl$_3$): δ 8.10-7.80 (m, 18H), 7.60-7.10 (m, 42H), 5.75 (s, 1H), 5.63 (t, J=9.6 Hz, 3H), 5.51 (t, J=9.6 Hz, 3H), 5.38 (t, J=8.0 Hz, 3H), 4.45-4.32 (m, 6H), 4.02 (d, J=8.0 Hz, 3H), 3.78 (d, J=9.6 Hz, 3H), 3.4-3.3 (m, 3H), 3.21-3.05 (m, 6H), 1.80-1.65 (m, 1H), 1.45-1.10 (m, 40H), 0.86 (t, J=6.8 Hz, 6H); $^{13}$C NMR (100 MHz, CDCl$_3$): δ 176.42, 166.07, 165.71, 165.06, 164.64, 133.71, 133.44, 133.27, 133.15, 129.96, 129.85, 129.76, 129.72, 129.62, 129.48, 129.03, 128.93, 128.86, 128.47, 128.34, 101.45, 72.64, 71.95, 69.57, 68.16, 62.96, 59.34, 53.47, 48.25, 32.83, 32.76, 31.99, 31.62, 29.98, 29.82, 29.45, 27.56, 27.36, 22.73, 22.72, 22.68, 14.14.

<3-5> Synthesis of TDT-C11

Deprotection was carried out according to the method of Example 1-5 and TDT-C11 having two C$_{11}$ alkyl groups was synthesized in a yield of 90%. $^1$H NMR (400 MHz, CD$_3$OD): δ 4.65-4.37 (m, 6H), 3.92-3.89 (m, 6H), 3.72-3.67 (m, 3H), 3.45-3.22 (m, 12H), 2.31-2.20 (m, 1H), 1.41-1.21 (m, 40H), 0.92 (t, J=6.8 Hz, 6H); $^{13}$C NMR (100 MHz, CD$_3$OD): δ 179.5, 104.8, 78.0, 75.1, 71.8, 69.4, 62.9, 61.1, 39.6, 34.3, 34.2, 33.2, 31.2, 31.0, 30.9, 30.8, 30.6, 28.6, 28.5, 23.8, 14.6. HRMS (EI): calcd. for C$_{46}$H$_{87}$NO$_{19}$[M+Na]$^+$ 980.5770, found 980.5766.

<Preparation Example 4> Synthesis of TDT-C12

<4-1> Synthesis of Dimethyl 2-Dodecylmalonate (Compound 4)

According to the dialkylated dimethylmalonate synthesis method of Example 1-1, dimethyl 2-dodecylmalonate (Compound 4) was synthesized in a yield of 89% using dodecyl iodide as alkyl iodide. $^1$H NMR (400 MHz, CDCl$_3$): δ 3.6 (s, 6H), 1.90-1.87 (m, 4H), 1.30-1.25 (m, 40H), 0.87 (t, J=7.2 Hz, 6H); $^{13}$C NMR (100 MHz, CDCl$_3$): δ 169.97, 61.53, 52.30, 32.11, 29.98, 29.94, 29.75, 29.60, 29.51, 29.4, 28.93, 27.53, 22.93, 14.40.

<4-2> Synthesis of Methyl 2-Dodecylundecanoate (Compound 8)

Demethoxy carbonylation was carried out according to the method of Examples 1-2 and methyl 2-dodecylundecanoate (Compound 8) was synthesized in a yield of 81%. $^1$H NMR (400 MHz, CDCl$_3$): δ 3.65 (s, 3H), 2.32-2.30 (m, 1H), 1.67-1.40 (m, 4H), 1.30-1.25 (m, 44H), 0.87 (t, J=7.2 Hz, 6H); $^{13}$C NMR (100 MHz, CDCl$_3$): δ 169.92, 61.51, 52.30, 32.15, 29.95, 29.96, 29.75, 29.61, 29.53, 29.41, 28.97, 27.53, 22.91, 14.43.

<4-3> Synthesis of N-(1,3-dihydroxy-2-(hydroxymethyl)propane-2-yl)-2-dodecylundecanamide (Compound 12)

Tris coupling was carried out according to the method of Example 1-3 and N-(1,3-dihydroxy-2-(hydroxymethyl)propane-2-yl)-2-dodecylundecanamide (Compound 12) was synthesized in a yield of 72%. $^1$H NMR (400 MHz, CDCl$_3$): δ 6.45 (s, 1H), 3.98 (br s, 3H), 3.64 (s, 6H), 2.11-2.05 (m, 1H), 1.63-1.39 (m, 4H), 1.38-1.20 (m, 40H), 0.88 (t, J=6.8 Hz, 6H)); $^{13}$C NMR (100 MHz, CDCl$_3$): δ 178.44, 131.13, 128.96, 62.51, 61.25, 48.17, 33.45, 32.02, 29.76, 29.70, 29.62, 29.42, 28.34, 28.11, 27.66, 22.81, 14.14.

<4-4> Synthesis of TDT-C12a

Glycosylation was carried out according to the method of Example 1-4 and TDT-C12a was synthesized in a yield of 70%. $^1$H NMR (400 MHz, CDCl$_3$): δ 8.10-7.80 (m, 18H), 7.60-7.10 (m, 42H), 5.75 (s, 1H), 5.63 (t, J=9.6 Hz, 3H), 5.51 (t, J=9.6 Hz, 3H), 5.38 (t, J=8.0 Hz, 3H), 4.45-4.32 (m, 6H), 4.02 (d, J=8.0 Hz, 3H), 3.78 (d, J=9.6 Hz, 3H), 3.4-3.3 (m, 3H), 3.21-3.05 (m, 6H), 3.02-2.90 (m, 2H), 1.80-1.65 (m, 1H), 1.45-1.05 (m, 36H), 0.86 (t, J=6.8 Hz, 6H); $^{13}$C NMR (100 MHz, CDCl$_3$): δ 176.56, 166.21, 165.84, 165.18, 164.75, 133.84, 133.57, 133.40, 133.29, 130.07, 129.96, 129.89, 129.70, 129.57, 129.15, 129.03, 128.97, 128.59, 128.47, 101.54, 72.73, 69.65, 68.25, 63.06, 59.42, 53.60, 48.35, 32.91, 32.85, 32.09, 30.05, 29.94, 29.87, 29.57, 29.55, 27.67, 27.46, 22.84, 14.29.

<4-5> Synthesis of TDT-C12

Deprotection was carried out according to the method of Example 1-5 and TDT-C12 having two C$_{12}$ alkyl groups was synthesized in a yield of 94%. $^1$H NMR (400 MHz, CD$_3$OD): δ 4.50-4.31 (m, 6H), 3.89-3.85 (m, 6H), 3.67-3.63 (m, 3H), 3.36-3.17 (m, 12H), 2.25-2.15 (m, 1H), 1.40-1.22 (m, 42H), 0.89 (t, J=6.8 Hz, 6H); $^{13}$C NMR (100 MHz, CD$_3$OD): δ 179.60, 104.88, 78.15, 75.24, 71.87, 69.47, 62.97, 61.24, 33.25, 31.23, 31.07, 31.03, 30.96, 30.84, 30.65, 28.73, 28.59, 23.89, 14.61. HRMS (EI): calcd. for C$_{48}$H$_{91}$NO$_{19}$[M+Na]$^+$ 1008.6083, found 1008.6086.

<Example 2> Synthesis of NDTs (Neopentyl Glycol-Derived Triglucosides)

Figure 3:
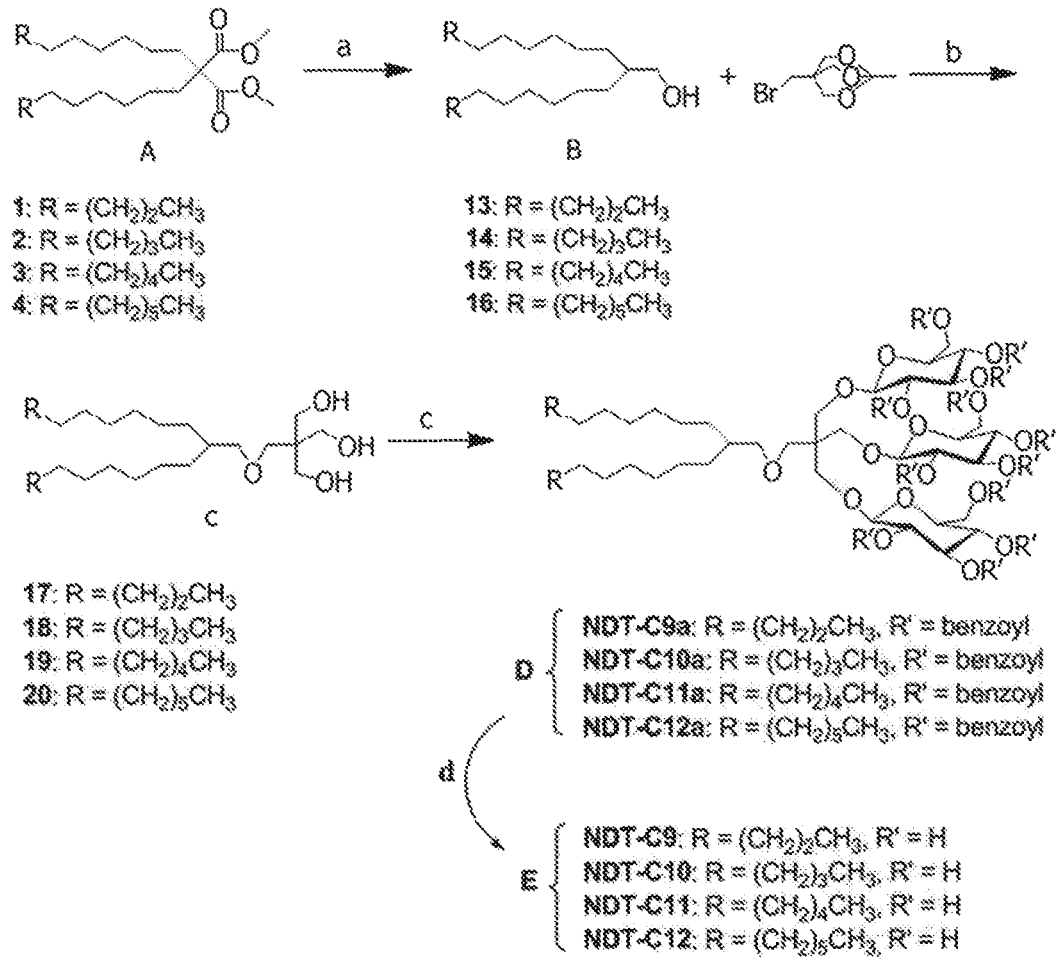
FIG. 3 illustrates a synthesis scheme of NDTs according to Example 2 of the present invention.
Figure 4:
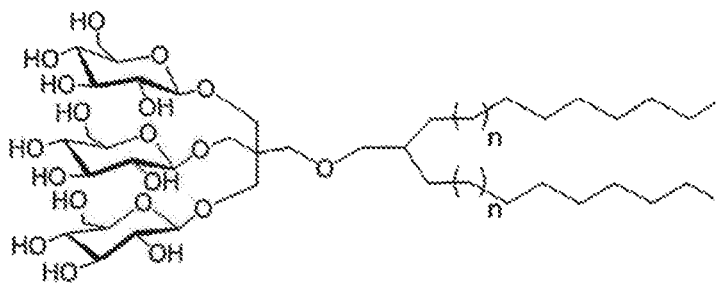
FIG. 4 illustrates chemical structures of NDTs according to the examples of the present invention.

A synthesis scheme of NDTs is illustrated in FIG. 3. The synthesis method of NDTs was the same as the TDTs synthesis method of Example 1, except for steps <1-2> and <1-3>. Accordingly, four types of neopentyl glycol-derived triglucosides (NDTs) were synthesized according to synthesis methods of the following steps <2-1> to <2-5>. The synthesized NDTs are illustrated in FIG. 4.

<2-1> General Synthesis Procedure of Dialkylated Dimethylmalonate (Synthesis of Compound A)

Dimethylmalonate (1.0 equiv.) was added dropwise to a DMSO solution, in which NaH (3.0 equiv.) was dissolved and which was kept cold using an ice bath. A resultant mixture was stirred until gas generation was terminated. Alkyl iodide (2.5 equiv.) was slowly added to the resultant solution. An obtained mixture was stirred for three hours at room temperature. The reaction was terminated by adding a cold 10% $NH_4Cl$ solution to the mixture. An obtained solution was washed with ethyl acetate twice. An organic ethyl acetate layer was collected and then washed with brine, followed by drying with anhydrous $Na_2SO_4$. A resultant product was concentrated with an organic solvent to obtain a residual oil. The residual oil was purified by column chromatography (EtOAc/hexane). As a result, a desired product, i.e., dialkylated dimethylmalonate (Compound A) was obtained as a colorless oil.

<2-2> General Procedure for Reduction of Dialkylated Ester Using LAH (Step a; A→B)

LiCl and distilled water were added to Compound A dissolved in DMSO. A resultant mixture was heated for 12 hours to be reluxed. A reacted mixture was cooled to room temperature and then distilled water was added thereto, followed by extracting with ethyl acetate. An organic layer was collected and then washed with brine, followed by drying with anhydrous $Na_2SO_4$. After performing concentration, a residual oil was obtained and used in a subsequent reduction step. A THF solution, in which $LiAlH_4$ (2.0 equiv.) was dissolved, was slowly added to a dialkylated mono methyl ester solution which was kept very cold. A resultant mixture was stirred at room temperature for six hours. The reaction was terminated by continuously adding MeOH, distilled water, and a 1 M HCl solution to the mixture at 0° C., followed by extracting with diethyl ether twice. An organic layer was bound and then washed with brine, followed by drying with anhydrous $Na_2SO_4$. A residue obtained after rotary evaporation was purified by silica gel column chromatography (EtOAc/hexane) to obtain Compound B as a desired product.

<2-3> General Synthesis Procedure for Dialkylated Tri-Ol (Step b; BC)

NaH (3.0 equiv.) was added to a solution including a dialkylated mono-ol (Compound B; 1.0 equiv.) dissolved in DMF. A resultant mixture was heated to 50° C. for 30 minutes. The mixture was cooled to room temperature and then 4-(bromomethyl)-1-methyl-2,6,7-trioxabicyclo[2.2.2]-octane (3.0 equiv.) dissolved in THF was slowly added thereto. An obtained mixture was heated to 100° C. for 24 hours. A reaction was terminated by adding methanol and then an organic solvent was removed from the mixture under reduced pressure. A residual solid was dissolved in a diethyl ether and this solution was washed with brine and dried with anhydrous $Na_2SO_4$. After concentrating an organic solvent, a residue was dissolved in a DCM/MeOH mixture. A few drops of strong HCl were added to this solution and then an obtained mixture was heated at 50° C. for four hours. A reacted mixture was neutralized with NaOH and concentrated. Subsequently, a residue was purified by column chromatography (EtOAc/hexane) to obtain Compound C as a desired product.

<2-4> General Procedure for Glycosylation (Step c; C→D)

Under a nitrogen atmosphere, a mixture of Compound C (1.0 equiv.), AgOTf (3.6 equiv.), and 2,4,6-collidine (1.0 equiv.) dissolved in anhydrous $CH_2Cl_2$ was stirred at −45° C. To this resultant suspension, a perbenzoylated glucosyl-bromide (3.6 equiv.) solution in $CH_2Cl_2$ was slowly added. Continuous stirring was performed at 45° C. for 30 minutes. Subsequently, the temperature of the reacted mixture was lowered to 0° C., followed by stirring at the same temperature for 1.5 hours. After completing the reaction (reaction completion was determined by TLC), pyridine was added to the reacted mixture, followed by diluting with $CH_2Cl_2$ and then filtering with Celite. A filtrate was continuously washed with an aqueous 1 M $Na_2S_2O_3$ solution, an aqueous 0.1 M HCl solution, and brine. An extracted organic layer was dried with anhydrous $Na_2SO_4$ and the solvent was removed therefrom by means of a rotary evaporator. A residue was purified by silica gel column chromatography (EtOAc/hexane) to obtain a desired product, i.e., Compound D, as a glassy solid.

<2-5> General Procedure for De-O-Benzoylation Under Zemplén Conditions (Step d; D→E)

An O-benzoylated (benzoylated) compound (Compound D) was dissolved in MeOH, and then 0.5 M NaOMe, as a methanolic solution, was added thereto in a necessary amount such that a final concentration of NaOMe became 0.05 M. A reacted mixture was stirred at room temperature for six hours and then neutralized with Amberlite IR-120 (H+ form) resin. The resin was removed from the reacted mixture by filtration and washed with MeOH, and then the solvent was removed from the reacted mixture under vacuum. A residue was purified by silica gel column chromatography (MeOH/$CH_2Cl_2$) to obtain a desired product, i.e., Compound E, as a white solid. The obtained Compound E was designated as (neopentyl glycol-derived triglucosides (NDTs).

<Preparation Example 5> Synthesis of NDT-C9

<5-1> Synthesis of dimethyl 2-nonylmalonate (Compound 1)

According to the dialkylated dimethylmalonate synthesis method of Example 2-1, dimethyl 2-nonylmalonate (Compound 1) was synthesized in a yield of 91% using nonyl iodide as alkyl iodide. $^1$H NMR (400 MHz, $CDCl_3$): δ 3.70 (s, 6H), 1.88-1.83 (m, 4H), 1.34-1.05 (m, 28H), 0.87 (t, J=7.2 Hz, 6H); $^{13}$C NMR (100 MHz, $CDCl_3$): δ 172.34, 57.56, 52.05, 31.83, 29.75, 29.43, 29.27, 29.23, 23.93, 22.61, 14.00.

<5-2> Synthesis of 2-Nonylundecan-1-Ol (Compound 13)

Reduction of dialkylated monoester was carried out according to the method of Example 2-2 and 2-nonylundecan-1-ol (Compound 13) was synthesized in a yield of 89%. $^1$H NMR (400 MHz, $CDCl_3$): δ 3.53 (d, J=5.6 Hz, 2H), 1.45 (t, J=5.6 Hz, 1H), 1.36-1.18 (m, 36H), 0.88 (t, J=6.4 Hz, 6H); $^{13}$C NMR (100 MHz, CDCl$_3$): δ 65.7, 40.5, 31.9, 30.9, 30.1, 29.6, 29.3, 26.9, 22.7, 14.1.

<5-3> Synthesis of 2-(((2-nonylundecyl)oxy) methyl)-2-(hydroxymethyl)propane-1,3-diol (Compound 17)

According to the method of Example 2-3, 2-(((2-nonylundecyl)oxy)methyl)-2-(hydroxymethyl)propane-1,3-diol (Compound 17) was synthesized in a yield of 44%. $^1$H NMR (400 MHz, CDCl$_3$): δ 3.72 (d, J=6.0 Hz, 6H), 3.43 (s, 2H), 3.3 (d, J=5.6 Hz, 2H), 2.72 (t, J=5.6 Hz, 3H), 1.61-1.51 (m, 1H), 1.36-1.18 (m, 32H), 0.88 (t, J=6.4 Hz, 6H); $^{13}$C NMR (100 MHz, CDCl$_3$): δ 72.06, 70.56, 68.91, 68.59, 67.91, 66.82, 63.58, 44.40, 43.09, 30.87, 28.68, 28.61, 28.46, 28.33, 25.19, 21.67, 13.10.

<5-4> Synthesis of NDT-C9

Glycosylation was carried out according to the method of Example 2-4 and NDT-C9a was synthesized in a yield of 50%. $^1$H NMR (400 MHz, CDCl$_3$): δ 8.10-7.80 (m, 18H), 7.60-7.10 (m, 42H), 5.63 (t, J=9.6 Hz, 3H), 5.51 (t, J=9.6 Hz, 3H), 5.38 (t, J=8.0 Hz, 3H), 4.45-4.32 (m, 6H), 4.02 (d, J=8.0 Hz, 3H), 3.78 (d, J=9.6 Hz, 3H), 3.4-3.3 (m, 3H), 3.21-3.05 (m, 6H), 3.02-2.90 (m, 2H), 1.42-1.36 (m, 1H), 1.35-1.01 (m, 32H), 0.86 (t, J=6.8 Hz, 6H); $^{13}$C NMR (100 MHz, CDCl$_3$): δ 166.1, 165.9, 165.2, 164.8, 133.6, 133.5, 133.3, 133.2, 130.1, 129.9, 129.8, 129.7, 129.1, 129.0, 128.5, 128.4, 101.6, 72.8, 72.1, 71.8, 69.8, 68.0, 63.2, 53.6, 45.2, 38.0, 32.1, 31.4, 31.3, 30.3, 29.9, 29.6, 27.0, 26.9, 22.8, 14.3.

<5-5> Synthesis of NDT-C9

Deprotection was carried out according to the method of Example 2-5 and NDT-C9 having two C$_9$ alkyl groups was synthesized in a yield of 90%. $^1$H NMR (400 MHz, CD$_3$OD): δ 4.50 (d, J=8.0 Hz, 3H), 4.21 (d, J=8.0 Hz, 3H), 3.88 (d, J=6.0 Hz, 3H), 3.77-3.74 (m, 6H), 3.58-3.52 (m, 2H), 3.40-3.25 (m, 10H), 3.10 (t, J=8.0 Hz, 3H), 1.48-1.40 (m, 1H), 1.30-1.10 (m, 32H), 0.80 (t, J=6.8 Hz, 6H); $^{13}$C NMR (100 MHz, CD$_3$OD): δ 133.64, 132.50, 130.01, 129.03, 105.20, 78.11, 77.90, 76.07, 75.26, 71.70, 70.73, 70.21, 62.85, 46.73, 39.49, 33.22, 32.63, 31.31, 31.30, 30.90, 30.62, 28.06, 23.87, 14.65. HRMS (EI): calcd. for C$_{43}$H$_{82}$O$_{19}$[M+Na]$^+$ 925.5348, found 925.5346.

<Preparation Example 6> Synthesis of NDT-C10

<6-1> Synthesis of Dimethyl 2-Decylmalonate (Compound 2)

According to the dialkylated dimethylmalonate synthesis method of Example 2-1, dimethyl 2-decylmalonate (Compound 2) was synthesized in a yield of 91% using decyl iodide as alkyl iodide. $^1$H NMR (400 MHz, CDCl$_3$): δ 3.70 (s, 6H), 1.88-1.83 (m, 4H), 1.34-1.25 (m, 32H), 0.87 (t, J=7.2 Hz, 6H); $^{13}$C NMR (100 MHz, CDCl$_3$): δ 172.55, 57.76, 52.25, 32.50, 32.03, 29.93, 29.71, 29.66, 29.45, 24.11, 23.66, 22.80, 14.20.

<6-2> Synthesis of 2-Decylundecan-1-Ol (Compound 14)

The reduction of dialkylated monoester was carried out according to the method of Example 2-2 and 2-decylundecan-1-ol (Compound 14) was synthesized in a yield of 88%. $^1$H NMR (400 MHz, CDCl$_3$): δ 3.53 (d, J=5.6 Hz, 2H), 1.45 (t, J=5.6 Hz, 1H), 1.36-1.18 (m, 36H), 0.88 (t, J=6.4 Hz, 6H); $^{13}$C NMR (100 MHz, CDCl$_3$): δ 65.6, 40.5, 31.9, 30.9, 30.1, 29.7, 29.3, 26.9, 22.7, 14.0.

<6-3> Synthesis of 2-(((2-decylundecyl)oxy) methyl)-2-(hydroxymethyl)propane-1,3-diol (Compound 18)

According to the method of Example 2-3, 2-(((2-decylundecyl)oxy)methyl)-2-(hydroxymethyl)propane-1,3-diol (Compound 18) was synthesized in a yield of 42%. $^1$H NMR (400 MHz, CDCl$_3$): δ 3.72 (d, J=6.0 Hz, 6H), 3.43 (s, 2H), 3.30 (d, J=5.6 Hz, 2H), 2.72 (t, J=5.6 Hz, 3H), 1.61-1.50 (m, 1H), 1.36-1.18 (m, 32H), 0.88 (t, J=6.4 Hz, 6H); $^{13}$C NMR (100 MHz, CDCl$_3$): δ 72.03, 70.51, 68.91, 68.59, 67.91, 66.82, 63.60, 44.40, 43.19, 30.87, 28.68, 28.61, 28.46, 28.33, 25.19, 21.67, 13.15.

<6-4> Synthesis of NDT-C10a

Glycosylation was carried out according to Example 2-4 and NDT-C10a was synthesized in a yield of 50%. $^1$H NMR (400 MHz, CDCl$_3$): δ 8.10-7.80 (m, 18H), 7.60-7.10 (m, 42H), 5.62 (t, J=9.6 Hz, 3H), 5.50 (t, J=9.6 Hz, 3H), 5.38 (t, J=8.0 Hz, 3H), 4.43-4.32 (m, 6H), 4.02 (d, J=8.0 Hz, 3H), 3.79 (d, J=9.6 Hz, 3H), 3.35 (t, J=4.8 Hz, 3H), 3.18-3.07 (m, 6H), 3.21-3.05 (m, 6H), 2.97-2.95 (m, 2H), 1.41-1.36 (m, 1H), 1.35-1.01 (m, 36H), 0.86 (t, J=6.8 Hz, 6H); $^{13}$C NMR (100 MHz, CDCl$_3$): δ 166.2, 165.9, 165.2, 164.9, 134.0, 133.8, 133.6, 133.5, 133.4, 133.2, 130.2, 130.1, 130.0, 129.9, 129.8, 129.1, 128.7, 128.6, 128.5, 101.6, 72.9, 72.8, 72.1, 71.8, 69.9, 63.3, 62.1, 32.1, 31.5, 30.4, 30.0, 29.9, 29.6, 27.0, 22.9, 14.3.

<6-5> Synthesis of NDT-C10

Deprotection was carried out according to the method of Example 2-5 and NDT-C10 having two Cm alkyl groups was synthesized in a yield of 93%. $^1$H NMR (400 MHz, CD$_3$OD): δ 4.30 (d, J=8.0 Hz, 3H), 3.98 (d, J=8.0 Hz, 3H), 3.84 (d, J=2 Hz, 3H), 3.70-3.60 (m, 6H), 3.48 (s, 2H), 3.34-3.21 (m, 10H), 3.19 (t, J=8.0 Hz, 3H), 1.48-1.40 (m, 1H), 1.30-1.10 (m, 36H), 0.80 (t, J=6.8 Hz, 6H); $^{13}$C NMR (100 MHz, CD$_3$OD): δ 105.23, 78.15, 77.94, 76.09, 75.29, 71.74, 70.21, 62.87, 46.76, 39.50, 33.22, 32.63, 31.30, 30.92, 30.64, 28.06, 23.88, 14.62. HRMS (EI): calcd. for C$_{45}$H$_{86}$O$_{19}$[M+Na]$^+$ 953.5661, found 953.5657.

<Preparation Example 7> Synthesis of NDT-C11

<7-1> Synthesis of Dimethyl 2-Undecylmalonate (Compound 3)

According to the dialkylated dimethylmalonate synthesis method of Example 2-1, dimethyl 2-undecylmalonate (Compound 3) was synthesized in a yield of 86% using undecyl iodide as alkyl iodide. $^1$H NMR (400 MHz, CDCl$_3$): δ 3.70 (s, 6H), 1.88-1.83 (m, 4H), 1.30-1.24 (m, 36H), 0.87 (t, J=7.2 Hz, 6H); $^{13}$C NMR (100 MHz, CDCl$_3$): δ 172.44, 57.71, 52.15, 51.21, 45.78, 32.63, 32.49, 32.03, 29.91, 29.74, 29.64, 29.47, 29.43, 27.58, 24.09, 22.79, 14.16.

<7-2> Synthesis of 2-Undecylundecan-1-Ol (Compound 15)

The reduction of dialkylated monoester was carried out according the method to Example 2-2 and 2-undecylundecan-1-ol (Compound 15) was synthesized in a yield of 76%. $^1$H NMR (400 MHz, CDCl$_3$): δ 3.53 (d, J=5.6 Hz, 2H), 1.45 (t, J=5.6 Hz, 1H), 1.36-1.18 (m, 40H), 0.88 (t, J=6.4 Hz, 6H); $^{13}$C NMR (100 MHz, CDCl$_3$): δ 65.7, 40.6, 32.1, 31.1, 30.3, 29.9, 29.8, 29.5, 27.0, 22.8, 14.2.

<7-3> Synthesis of 2-(((2-undecylundecyl)oxy)methyl)-2-(hydroxymethyl)propane-1,3-diol (Compound 19)

According to the method of Example 2-3, 2#(2-undecylundecyl)oxy)methyl)-2-(hydroxymethyl)propane-1,3-diol (Compound 19) was synthesized in a yield of 40%. $^1$H NMR (400 MHz, CDCl$_3$): δ 3.72 (s, 6H), 3.44 (s, 2H), 3.31 (d, J=5.6 Hz, 2H), 2.52 (s, 3H), 1.59-1.41 (m, 1H), 1.36-1.18 (m, 40H), 0.88 (t, J=6.8 Hz, 6H); $^{13}$C NMR (100 MHz, CDCl$_3$): δ 73.26, 71.77, 70.10, 69.78, 69.11, 68.03, 64.72, 45.60, 45.11, 32.07, 29.88, 29.81, 29.66, 29.53, 26.39, 22.87, 14.30.

<7-4> Synthesis of NDT-C11a

Glycosylation was carried out according to the method of Example 2-4 and NDT-C11a was synthesized in a yield of 47%. $^1$H NMR (400 MHz, CDCl$_3$): δ 8.04-7.80 (m, 24H), 7.55-7.37 (m, 36H), 5.62 (t, J=9.6 Hz, 3H), 5.50 (t, J=9.6 Hz, 3H), 5.37 (t, J=8.0 Hz, 3H), 4.39-4.34 (m, 6H), 4.01 (d, J=8.0 Hz, 3H), 3.78 (d, J=9.6 Hz, 3H), 3.37-3.33 (m, 3H), 3.13-3.10 (m, 6H), 2.96-2.94 (m, 2H), 1.43-1.37 (m, 1H), 1.36-1.02 (m, 40H), 0.86 (t, J=6.8 Hz, 6H); $^{13}$C NMR (100 MHz, CDCl$_3$): δ 166.2, 165.9, 165.4, 164.8, 133.6, 133.5, 133.3, 130.2, 130.1, 130.0, 129.9, 129.8, 129.1, 129.0, 128.6, 128.5, 101.5, 90.6, 72.8, 72.3, 72.0, 71.8, 71.7, 70.2, 69.9, 69.8, 69.6, 68.2, 68.0, 63.2, 63.0, 45.5, 45.0, 32.0, 29.8, 29.7, 29.5, 26.4, 22.8, 14.3.

<7-5> Synthesis of NDT-C11

Deprotection was carried out according to the method of Example 2-5 and NDT-C11 having two C$_{11}$ alkyl groups was synthesized in a yield of 90%. $^1$H NMR (400 MHz, CD$_3$OD): δ 4.30 (d, J=8.0 Hz, 3H), 3.98 (d, J=10.0 Hz, 3H), 3.84 (d, J=12 Hz, 3H), 3.69-3.62 (m, 6H), 3.48 (s, 2H), 3.34-3.21 (m, 10H), 3.18 (t, J=8.0 Hz, 3H), 1.56-1.50 (m, 1H), 1.36-1.20 (m, 40H), 0.89 (t, J=6.8 Hz, 6H); $^{13}$C NMR (100 MHz, CD$_3$OD): δ 105.0, 78.0, 77.8, 75.2, 72.6, 71.1, 70.8, 70.7, 70.1, 69.9, 69.7, 62.7, 46.7, 46.5, 39.5, 33.1, 31.0, 30.8, 30.6, 27.5, 23.8, 14.6. HRMS (EI): calcd. for C$_{47}$H$_{90}$O$_{19}$[M+Na]$^+$ 981.5974, found 981.5977.

<Preparation Example 8> Synthesis of NDT-C12

<8-1> Synthesis of Dimethyl 2-Dodecylmalonate (Compound 4)

According to the dialkylated dimethylmalonate synthesis method of Example 2-1, dimethyl 2-dodecylmalonate (Compound 4) was synthesized in a yield of 89% using dodecyl iodide as alkyl iodide. $^1$H NMR (400 MHz, CDCl$_3$): δ 3.6 (s, 6H), 1.90-1.87 (m, 4H), 1.30-1.25 (m, 40H), 0.87 (t, J=7.2 Hz, 6H); $^{13}$C NMR (100 MHz, CDCl$_3$): δ 169.97, 61.53, 52.30, 32.11, 29.98, 29.94, 29.75, 29.60, 29.51, 29.4, 28.93, 27.53, 22.93, 14.40.

<8-2> Synthesis of 2-Dodecylundecan-1-Ol (Compound 16)

Reduction of dialkylated monoester was carried out according to the method of Example 2-2 and 2-dodecylundecan-1-ol (Compound 16) was synthesized in a yield of 83%. $^1$H NMR (400 MHz, CDCl$_3$): δ 3.53 (d, J=5.6 Hz, 2H), 1.45 (t, J=5.6 Hz, 1H), 1.36-1.18 (m, 44H), 0.88 (t, J=6.4 Hz, 6H); $^{13}$C NMR (100 MHz, CDCl$_3$): δ 65.7, 40.5, 31.9, 30.9, 30.1, 29.6, 29.3, 26.9, 22.7, 14.1.

<8-3> Synthesis of 2-(((2-dodecylundecyl)oxy)methyl)-2-(hydroxymethyl)propane-1,3-diol (Compound 20)

According to the method of Example 2-3, 2-(((2-dodecylundecyl)oxy)methyl)-2-(hydroxymethyl)propane-1,3-diol (Compound 17) was synthesized in a yield of 44%. $^1$H NMR (400 MHz, CDCl$_3$): δ 3.70 (s, 6H), 3.42 (s, 2H), 3.30 (d, J=5.6 Hz, 2H), 2.96 (s, 3H), 1.60-1.51 (m, 1H), 1.36-1.18 (m, 44H), 0.88 (t, J=6.8 Hz, 6H); $^{13}$C NMR (100 MHz, CDCl$_3$): δ 73.05, 71.77, 71.10, 69.78, 69.11, 68.03, 66.31, 64.72, 45.60, 45.11, 32.07, 29.88, 29.81, 29.66, 29.53, 28.64, 26.39, 21.87, 14.30.

<8-4> Synthesis of NDT-C12a

Glycosylation was carried out according to the method of Example 2-4 and NDT-C12a was synthesized in a yield of 65%. $^1$H NMR (400 MHz, CDCl$_3$): δ 8.04-7.80 (m, 24H), 7.55-7.37 (m, 36H), 5.62 (t, J=9.6 Hz, 3H), 5.50 (t, J=9.6 Hz, 3H), 5.37 (t, J=8.0 Hz, 3H), 4.39-4.34 (m, 6H), 4.01 (d, J=8.0 Hz, 3H), 3.78 (d, J=9.6 Hz, 3H), 3.37-3.33 (m, 3H), 3.13-3.10 (m, 6H), 2.96-2.94 (m, 2H), 1.42-1.37 (m, 1H), 1.36-1.02 (m, 40H), 0.86 (t, J=6.8 Hz, 6H)); $^{13}$C NMR (100 MHz, CDCl$_3$): δ 166.39, 166.09, 165.96, 165.90, 165.35, 165.14, 164.75, 133.55, 133.43, 133.27, 133.16, 133.12, 130.10, 129.95, 129.89, 129.86, 129.75, 129.64, 129.20, 129.03, 128.96, 128.88, 128.47, 128.36, 101.53, 92.31, 90.50, 74.65, 74.13, 72.72, 72.34, 72.01, 71.70, 70.29, 69.55, 68.48, 67.70, 63.18, 62.93, 45.13, 37.97, 31.98, 30.25, 29.85, 29.75, 29.44, 26.90, 26.86, 22.74, 14.19.

<8-5> Synthesis of NDT-C12

Deprotection was carried out according to the method of Example 2-5 and NDT-C12 having two C$_{12}$ alkyl groups was synthesized in a yield of 90%. $^1$H NMR (400 MHz, CD$_3$OD): δ 4.30 (d, J=8.0 Hz, 3H), 3.98 (d, J=10.0 Hz, 3H), 3.84 (d, J=12 Hz, 3H), 3.69-3.62 (m, 6H), 3.48 (s, 2H), 3.34-3.21 (m, 10H), 3.18 (t, J=8.0 Hz, 3H), 1.56-1.50 (m, 1H), 1.36-1.20 (m, 44H), 0.89 (t, J=6.8 Hz, 6H); $^{13}$C NMR (100 MHz, CD$_3$OD): δ 105.1, 78.0, 77.7, 76.0, 75.1, 71.5, 71.3, 70.6, 70.1, 62.7, 46.6, 39.3, 33.1, 32.5, 31.2, 30.8, 30.5, 27.9, 23.8, 14.6. HRMS (EI): calcd. for C$_{49}$H$_{94}$O$_{19}$[M+Na]$^+$ 1009.6287, found 1009.6290.

<Example 3> Characteristics of TDTs and NDTs

So as to investigate characteristics of TDTs of Preparation Examples 1 to 4 synthesized according to the synthesis method of Example 1 and NDTs of Preparation Examples 5 to 8 synthesized according to the synthesis method of Example 2, molecular weights (M.W.) and critical micellar concentrations (CMCs) of TDTs and NDTs and hydrodynamic radii (R$_h$) of formed micelles were measured.

In particular, critical micellar concentrations (CMCs) were measured using hydrophobic fluorescence staining and diphenylhexatriene (DPH), and hydrodynamic radii (R$_h$) of micelles formed of each material were measured by a dynamic light scattering (DLS) experiment. Measured results are compared to values of DDM as an existing amphipathic molecule (detergent). Results are summarized in Table 1.

TABLE 1

| Detergents | M.W. | CMC (μM) | CMC (% by weight) | Rh (nm) |
|---|---|---|---|---|
| TDT-C9 | 902.1 | 47 ± 1.5 | 0.0042 ± 0.0001 | 3.4 ± 0.4 |
| TDT-C10 | 930.1 | 14 ± 1.0 | 0.0013 ± 0.0001 | 4.5 ± 0.2 |
| TDT-C11 | 958.2 | 11 ± 1.5 | 0.0011 ± 0.0001 | 37 ± 8.0 |
| TDT-C12 | 986.2 | 6.0 ± 0.1 | 0.0006 ± 0.0000 | 53 ± 1.2 |
| NDT-C9 | 903.1 | 26 ± 4.0 | 0.0023 ± 0.0004 | 3.1 ± 0.1 |
| NDT-C10 | 931.2 | 12 ± 0.5 | 0.0011 ± 0.0000 | 3.2 ± 0.1 |
| NDT-C11 | 959.2 | 6.1 ± 1.8 | 0.0005 ± 0.0002 | 3.5 ± 0.0 |
| NDT-C12 | 987.3 | 2.4 ± 0.9 | 0.0002 ± 0.0001 | 3.8 ± 0.4 |
| DDM | 510.1 | ~170 | ~0.0087 | 3.4 ± 0.0 |

CMC values of TDTs and NDTs are much smaller than those of DDM. CMC values of TDT-C12 and NDT-C12 which have the longest alkyl chain (C12) were at least 100× smaller than those of DDM. Accordingly, it can be confirmed that small amounts of TDTs and NDTs easily form micelles, thus having better solubility than DDM. In addition, the CMC values of TDTs are greater than those of NDTs, alkyl chains of which are the same as those of TDTs. In addition, the CMC values of TDTs and NDTs tend to decrease with increasing alkyl chain length. This can be interpreted as occurring since hydrophobicity increases with increasing alkyl chain length.

The sizes of the micelles formed of NDTs are 3.1 to 3.8 nm which are almost similar to DDM. On the other hand, the sizes of the micelles formed of TDTs range from 3.4 to 52.5 nm which are broader than the size range of NDTs. Therefore, it can be confirmed that a small difference between chemical structures of TDTs and NDTs (i.e., amide or ether) considerably affects self-aggregation patterns thereof in an aqueous solution. The sizes of micelles formed of TDTs and NDTs increase with increasing alkyl chain lengths.

Figure 5A:
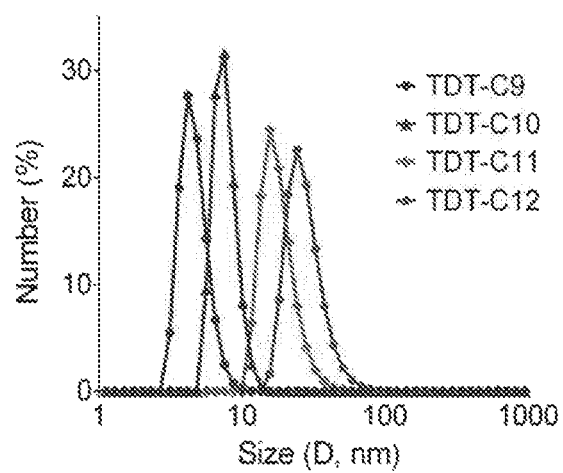
FIGS. 5a and 5B illustrate size (diameter (D), nm) distribution graphs of micelles formed of TDTs or NDTs.
Figure 5B:
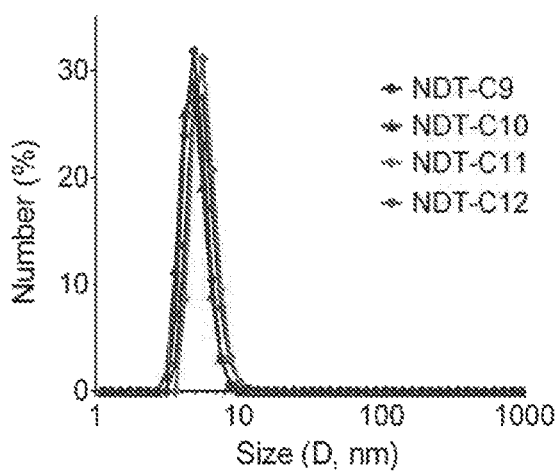

Meanwhile, size distributions of the micelles formed of TDTs and NDTs were measured using DLS. Results are illustrated in FIG. 5. TDTs or NDTs were respectively used in an amount of 0.5% by weight. As a result, micelles of TDTs or NDTs were measured as forming a single community.

From these results, it can be confirmed that, since TDTs or NDTs of the present invention have CMC values smaller than DDM, small amounts of TDTs or NDTs easily form micelles and thus self-assembly tendencies thereof are much greater than DDM. In addition, it can be confirmed that, since the sizes of the micelles formed of TDTs are greatly varied depending upon the lengths of alkyl chains, whereas the sizes of the micelles formed of NDTs are similar to that of DDM, self-aggregation patterns of TDTs and NDTs are different due to small structural differences therebetween.

<Example 4> Evaluation of Membrane Protein (UapA) Structural Stabilization Ability of TDTs and NDT Experiments to measure the structural stability of a uric acid-xanthine/H+ symporter (UapA) due to TDTs or NDTs in an aqueous solution were conducted. The structural stability of UapA was measured using CPM assay, and the concentrations of TDTs, NDTs, and DDM concentration were CMC+0.04% by weight.

In particular, UapA protein is a uric acid-xanthine/H+ symporter in Aspergillus nidulans). The stability of the protein was measured using N-[4-(7-Diethylamino-4-methyl-3-coumarinyl)phenyl]maleimide (CPM), as a sulfhydryl-specific fluorophore, by means of a fluorescence spectrophotometer. A free sulfhydryl group of a cysteine residue is present within the center of the protein but may be present near a solvent due to unfolding of the protein. CPM becomes fluorescent by reaction with free thiol and, accordingly, functions as a sensor of unfolding. To measure heat stability, UapAG411V$_{1-11}$ was GFP-fused to be expressed in a Saccharomyces cerevisiae FGY217 strain and separated in a sample buffer (20 mM Tris (pH 7.5), 150 mM NaCl, 0.03% DDM, 1 mM xanthine), according to the method disclosed by J. Leung, et al. (Mol. Membr. Biol. 2013, 30, 32-42). The UapA protein was concentrated to about 10 mg/ml using a 100 kD molecular weight cut off filter (Millipore). The concentrated protein was diluted to a concentration of CMC+0.04% by weight or CMC+0.2% by weight with a buffer including DDM, TDTs, or NDTs in a ratio of 1:150 in a Greiner 96-well plate. A CPM dye (Invitrogen) stored in DMSO (Sigma) was diluted with a buffer for a dye (20 mM Tris (pH 7.5), 150 mM NaCl, 0.03% DDM, 5 mM EDTA) and 3 μl of the diluted dye was added under each protein test condition. The reaction was monitored at 40° C. for 120 minutes by means of a microplate spectrofluorometer. So as to calculate a ratio of folded proteins relative to remaining proteins after being maintained at 40° C. for 130 minutes, relative maximum fluorescence was used. The relative amounts of the folded proteins were time-dependently represented using GraphPad Prism.

Figure 6A:
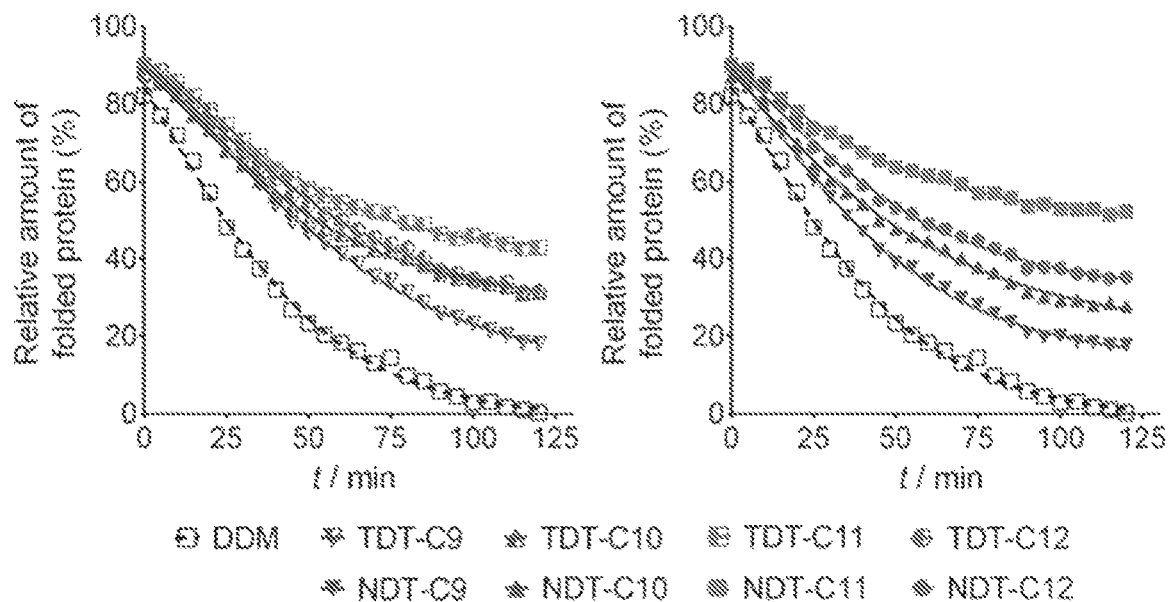
FIGS. 6a and 6b illustrate the structural stability, which is measured using CPM assay, of UapA protein by (a) TDTs or (b) NDTs used in a concentration of CMC+0.04% by weight in an aqueous solution (average standard deviation (n=2) of DDM, TDT-C9, TDT-C10, TDT-C11, TDT-C12, NDT-C9, NDT-C10, NDT-C11 and NDT-C12 which are respectively 4.9, 9.3, 2.3, 5.8, 6.1, 2.7, 9.4, 10.2, 9.5).
Figure 6B:
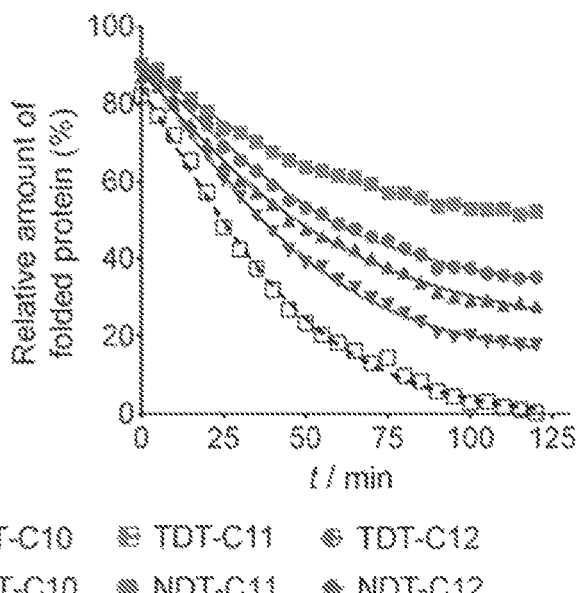

FIG. 6 illustrates the structural stability measurement results of UapA protein by TDTs (FIG. 6a) or NDTs (FIG. 6b) when the amphipathic molecules are used in a concentration of CMC+0.04% by weight. The amount of the UapA protein folded by TDTs or NDTs was greater than that by DDM. Protein (UapA) folding states by TDTs having an amide linkage were better maintained than that of DDM. In addition, UapA stability by NDTs was superior to DDM and protein stabilization effects of NDTs were superior to those of TDTs. In particular, the protein stabilization effect of NDT-C11 among all amphipathic molecules was most excellent.

Figure 7A:
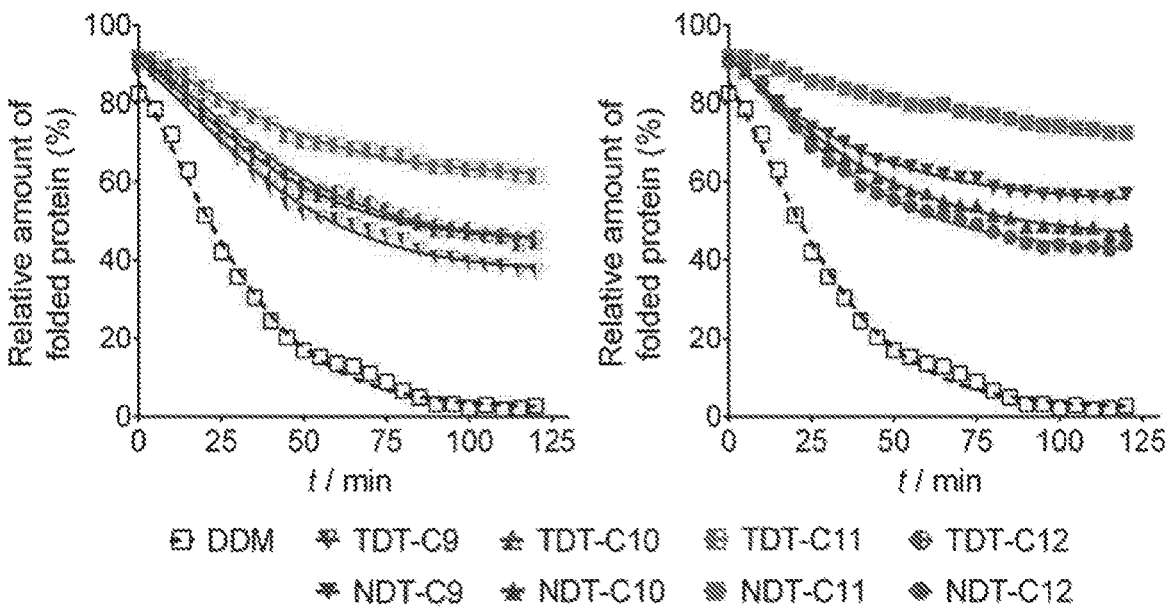
FIGS. 7a and 7b illustrate the structural stability, which is measured using CPM assay, of UapA protein by (a) TDTs or (b) NDTs used in a concentration of CMC+0.2% by weight (average standard deviation (n=2) of DDM, TDT-C9, TDT-C10, TDT-C11, TDT-C12, NDT-C9, NDT-C10, NDT-C11 and NDT-C12 are respectively 3.8, 5.0, 10.5, 14.6, 3.6, 7.1, 5.1, 3.0, 8.9).
Figure 7B:
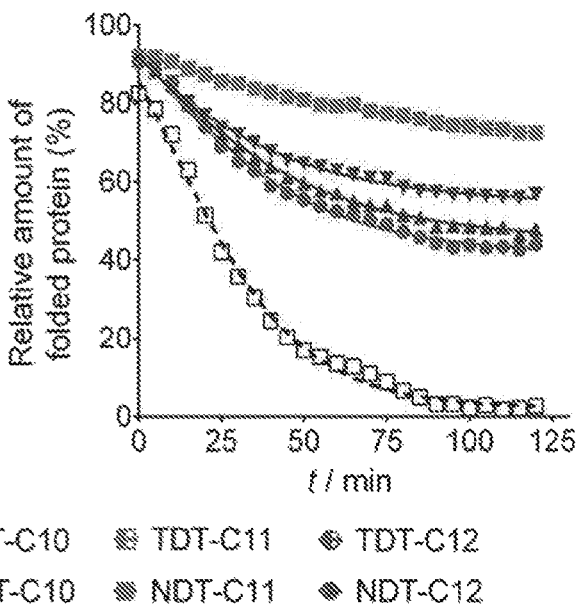

FIG. 7 illustrates the structural stability measurement results of UapA protein by TDTs (FIG. 7a) or NDTs (FIG. 7b) when the amphipathic molecules are used in a concentration of CMC+0.2% by weight. The overall trend was similar to that at the concentration of CMC+0.04% by weight, but protein stability was varied greatly depending upon linkage types (amide or ether linkage) of the amphipathic molecules. With regard to protein stability, TDTs were remarkably superior to DDM and NDTs were superior to TDTs. In particular, the UapA protein stabilization effect of NDT-C11 was most excellent.

Figure 8:
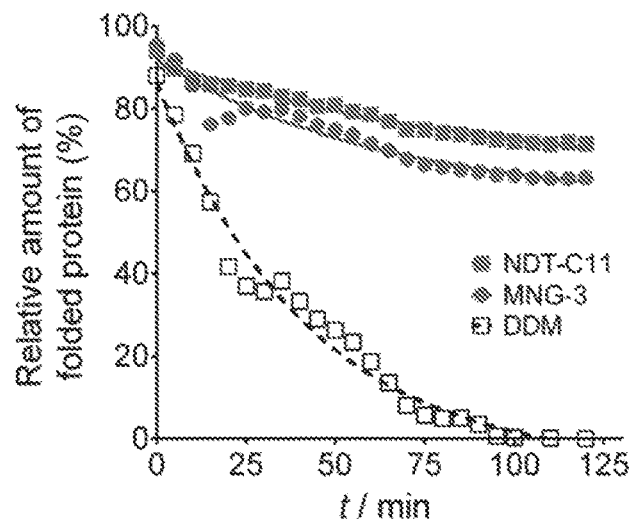
FIG. 8 illustrates the structural stability of UapA proteins measured using CPM assay when NDT-C11, MNG-3, and DDM are used in an amount of CMC+0.2% by weight.

FIG. 8 illustrates the structural stability measurement results of UapA protein by NDT-C$_{11}$, MNG-3, and DDM when the amphipathic molecules are used at a concentration of CMC+0.2% by weight. In maintaining a folding state of the UapA protein, the effect of NDT-C11 was superior to those of MNG-3, the effect of which is most excellent among maltose-neopentyl glycol amphiphiles (MNGs) (See Nat. Methods., 2010, 7, 1003-1008, published by the present inventors).

From these results, it can be confirmed that UapA structural stabilization ability of TDTs and NDTs is excellent even at a high concentration. In particular, it can be confirmed that, since effects of NDTs are superior to those of TDTs in maintaining a UapA protein folding state, NDTs may be used to extract or stabilize a membrane protein.

<Example 5> Evaluation of Membrane Protein (MelB) Structural Stabilization Ability by TDTs and NDTs <5-1> SDS-PAGE and Western Immunoblotting Experiments to measure the extraction efficiency and structural stability of a *Salmonella typhimurium* melibiose permease (MelB) protein by TDTs or NDTs were conducted. The MelB protein was extracted using TDTs, NDTs, or DDM and then the amounts and structures of extracted proteins were quantitatively analyzed by SDS-PAGE and western immunoblotting. The concentrations of the used amphipathic molecules were 1.5% by weight. Protein extraction was carried out at four temperatures (0, 45, 55 or 65° C.) for 90 minutes to simultaneously evaluate the protein extraction efficiency and stabilization ability of the amphipathic molecules.

In particular, in accordance with a method disclosed in a paper (P. S. Chae, et al., *Chemistry.* 2013, 19, 15645-15651) published by the present inventors, a protein ($MelB_{St}$) was produced using a pK95AHB/WT $MelB_{St}$/CH10 plasmid and a *Salmonella typhimurium* DW2 cell (melB and lacZY) to encode wild-type MelB having a 10-His tag at a C-terminal. In accordance with a method disclosed in a paper (*Nat. Commun.* 2014, 5, 3009) published by A. S. Ethayathulla, et al., cell proliferation and membrane preparation was carried out. Protein analysis was performed using a Micro BCA kit (Thermo Scientific, Rockford, Ill.). So as to measure the solubilization/stability of $MelB_{St}$, a membrane sample including $MelB_{St}$ (final protein concentration of 10 mg/mL) was mixed with a solubilization buffer (20 mM sodium phosphate, pH 7.5, 200 mM NaCl, 10% glycerol, and 20 mM melibiose) and 1.5% (w/v) DDM, TDTs or NDTs. An extracted product was incubated at four temperatures (0, 45, 55 and 65° C.) for 90 minutes. Ultracentrifugation was carried out for 45 minutes at 4° C. and 355,590 g by means of a Beckman Optima™ MAX ultracentrifuge and a TLA-100 rotor. Subsequently, 20 μg of a protein was separated by SDS-16% PAGE and then subjected to immunoblotting with a Penta-His-HRP antibody (Qiagen, Germantown, Md.).

Figure 9:
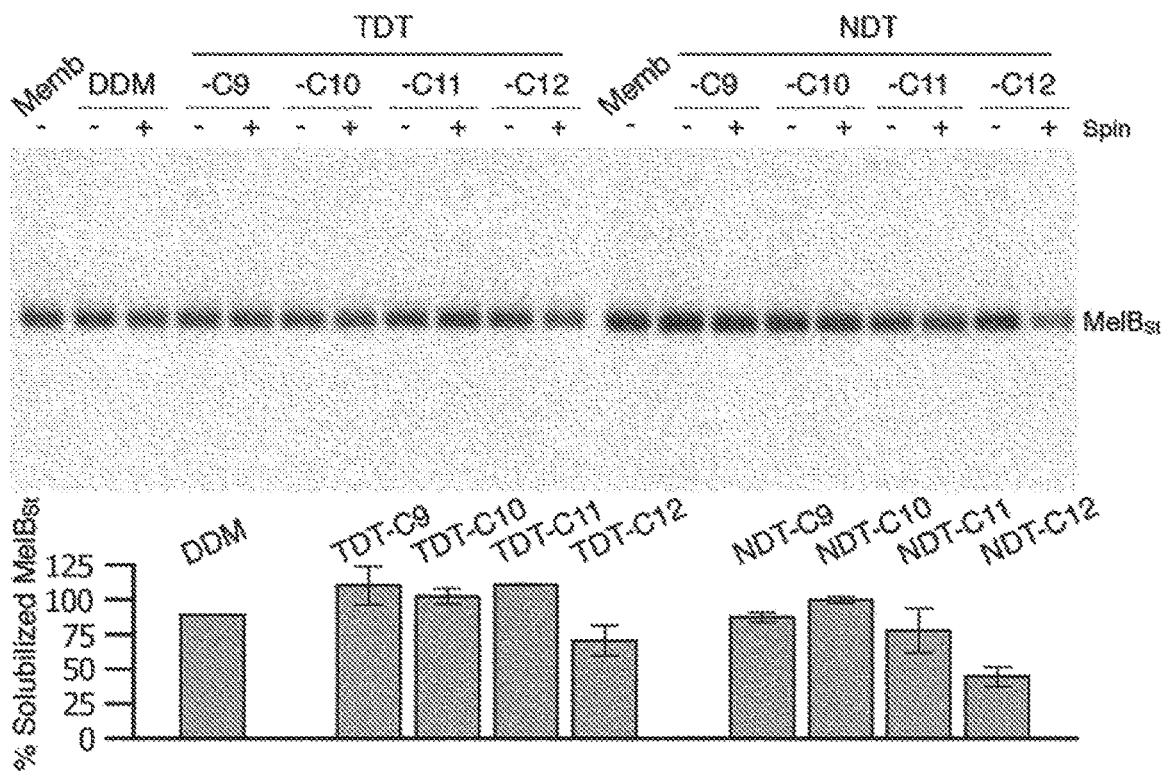
FIG. 9 illustrates extraction efficiencies and structural stability of MelB proteins, which are formed of TDTs or NDTs, at 0° C. measured using SDS-PAGE and western immunoblotting.

FIG. 9 illustrates SDS-PAGE and western immunoblotting results performed at 0° C. All TDTs and NDTs, except for TDT-C12 and NDT-C12, exhibited superior efficiency in extracting the MelB protein from a membrane at 0° C. Slightly decreased solubilization effects of TDT-C12 and NDT-C12 are considered to be caused by a tendency thereof to form hydrogels at low temperature.

Figure 10:
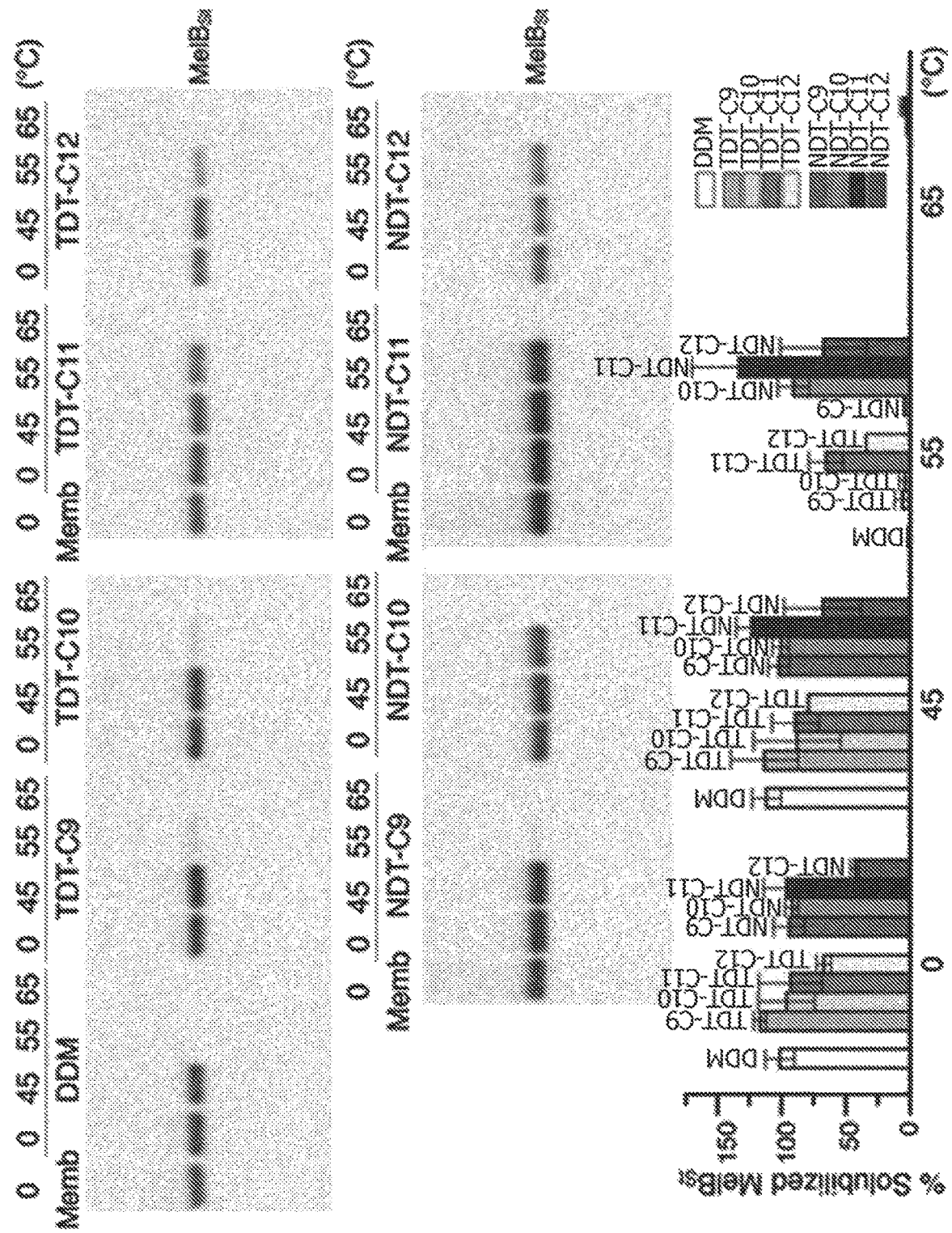
FIG. 10 illustrates extraction efficiencies and structural stability of MelB proteins, which are formed of TDTs or NDTs, at 0, 45, 55 and 65° C. measured using SDS-PAGE and western immunoblotting.

FIG. 10 illustrates SDS-PAGE and western immunoblotting results at 0, 45, 55, and 65° C. The amount of MelB stabilized by TDTs or NDTs after being incubated at 45° C. for 90 minutes is similar to the amount dissolved by DDM. In particular, it is illustrated that MelB protein solubilization effects of TDT-C12 and NDT-C12 increase with elevating temperature. This result is considered to be caused by a trend of decreased hydrogel formation with elevating temperature. At 55° C., MelB dissolved by DDM is hardly detected, but, in the case of all TDTs, MelB proteins dissolved by TDTs are detected. In particular, the amount of a protein dissolved by TDT-C11 is 65%. All NDTs exhibit MelB protein solubilization ability superior to TDTs or DDM. Thereamong, the protein solubilization ability of NDT-C11 is most excellent.

<5-2> Forster Resonance Energy Transfer (FRET) Measurement

So as to investigate functional states of MelB proteins dissolved by amphipathic molecules, Førster resonance energy transfer (FRET) to 2'-(N-dansyl)aminoalkyl-1-thio-β-D-galactopyranoside ($D^2G$), as a fluorescence ligand, was measured in tryptophan (Trp). A principle of this experiment is as follows: the MelB protein coupled with $D^2G$ exhibits fluorescence by energy transfer due to a close distance between a FRET pair (Trp and $D^2G$). However, if a protein dissolved by an amphipathic molecule has activity, melibiose substitutes for the coupled $D^2G$ molecule upon addition of the melibiose and thus energy transfer no longer occurs, thereby decreasing fluorescence intensity. Accordingly, the activity of the MelB protein dissolved in DDM or NDT-C11 can be determined by whether reversal of $D^2G$ FRET occurs due to melibiose in Trp. Therefore, the FRET measurement method is an efficient method to measure the membrane protein structural stabilization ability of an amphipathic molecule.

In particular, a right-side-out (RSO) membrane vesicle was prepared by osmotic lysis of an *E. coli* DW2 cell containing $MelB_{St}$ or $MelB_{Ec}$ and re-suspended with 100 mM $KP_i$ (pH 7.5), followed by storing at −80° C. $D^2G$ was provided by H. Ronald Kaback and Gerard Leblanc. A protein concentration of an RSO membrane vesicle in 100 mM $KP_i$, pH 7.5, and 50 mM NaCl was 1 mg/ml concentration. This RSO membrane vesicle was solubilized with DDM or NDT-C11 (1.0% by weight) at 23° C. for 30 minutes, and ultracentrifugation was performed at 4° C. and >300,000 g for 45 minutes by means of a TLA 120.2 rotor. A lysed fraction (supernatant) was subjected to Trp→$D^2G$ FRET measurement by means of an Amico-Bowman Series 2 (AB2) spectrofluorometer. A Trp residue was excited at 290 nm. An emission wavelength of $MelB_{Ec}$ was measured at 465 nm and an emission wavelength of $MelB_{St}$ was measured at 490 nm. One minute after FRET measurement initiation, 10 μM $D^2G$ was added. After two minutes, a large amount of melibiose or the same amount of water was added thereto. A protein solubilized with the amphipathic molecule couples with $D^2G$ upon addition of $D^2G$ and, when a large amount of melibiose is added in this state, different results are exhibited depending upon a degree of a structural deformation of a protein. Since a protein having a stable structure has strong binding force to melibiose and, accordingly, binds to an active site of melibiose instead of $D^2G$, $D^2G$ is released from a binding site and thus FRET no longer occurs. Accordingly, fluorescence intensity is decreased. On the other hand, in the case of a protein having a deformed structure, binding force thereof to additionally added melibiose is lost and thus FRET intensity is not changed.

Figure 11:
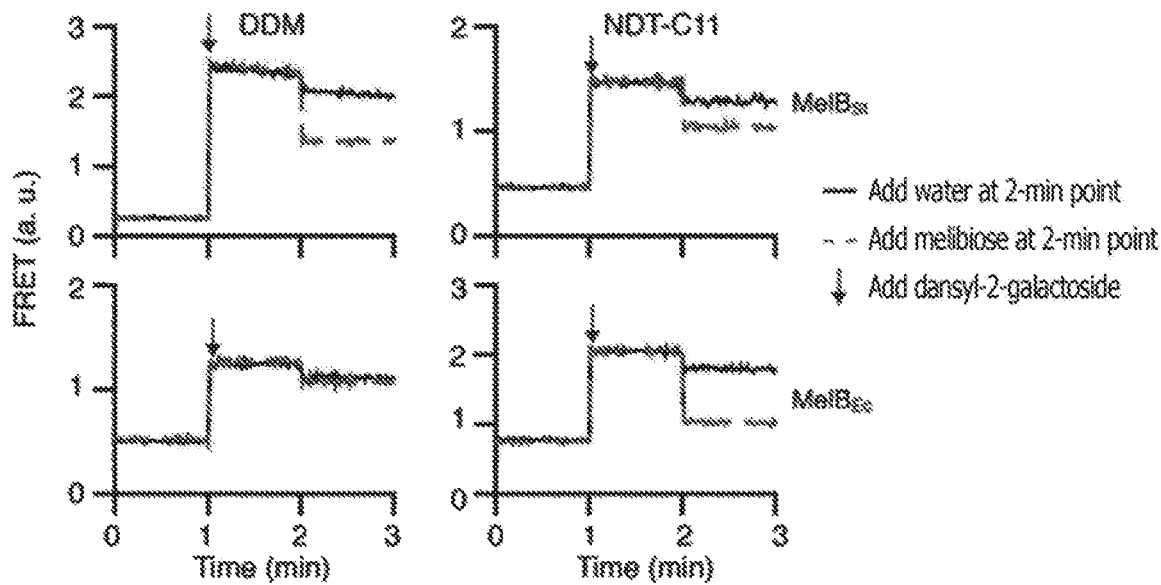
FIG. 11 illustrates FRET measurement results to determine the functional stability of MelB proteins ($MelB_{St}$ or $MelB_{Ec}$) dissolved by DDM or NDT-C11.

FIG. 11 illustrates FRET results of MelB proteins dissolved in DDM or NDT-C11. DDM and NDT-C11 enable production of functional $MelB_{St}$ proteins, which is similar to a previous research result in which MNG-3 is used (See *Biochemistry* 2015, 54, 5849-5855, published by the present inventors). To distinguish efficiencies of amphipathic molecules, $MelB_{Ec}$, which is less stable than $MelB_{St}$, was used as a comparison group. When extraction was performed with DDM, binding force between the $MelB_{Ec}$ protein and melibiose was completely lost. On the other hand, in the case of $MelB_{Ec}$ solubilized with NDT-C11, the functionality of the $MelB_{Ec}$ was effectively maintained. Such a result shows that NDT-C11 may allow melibiose coupling activity maintenance in all of $MelB_{St}$ and $MelB_{Ec}$, whereas DDM is effective only in more stable $MelB_{St}$.

From such results, it can be confirmed that the MelB protein stabilization ability of TDTs or NDTs of the present invention is superior to that of DDM and the MelB protein extraction efficiencies of TDTs or NDTs of the present invention are excellent.

<Example 6> Evaluation of Membrane Protein (LeuT) Structural Stabilization Ability of TDTs and NDTs <6-1> Measurement of Stability of LeuT Protein by NDTs Experiments to measure the structural stability of a leucine transporter (LeuT) protein by TDTs or NDTs were conducted. LeuT protein activity was measured by scintillation proximity assay (SPA) utilizing [$^3$H]-Leu as a ligand. The concentration of TDTs, NDTs, or DDM was (a) CMC+0.04% by weight, or (b) CMC+0.02% by weight.

In particular, the LeuT stability measurement experiments were conducted according to the following methods. Depending upon the results of UapA and MelB, only TDT-C11, TDT-C12, NDT-C10, NDT-C11 and NDT-C12 among the amphipathic molecules according to the present invention were selectively used. In accordance with a method disclosed in a paper published by G. Deckert, et al. (*Nature* 1998, 392, 353-358), a wild-type leucine transporter (LeuT) was purified from *Aquifex aeolicus*. LeuT is expressed in *E. coli* C41 (DE3) transformed with pET16b encoding a C-terminal 8×His-tagged transporter (the expression plasmid was provided by Dr E. Gouaux, Vollum Institute, Portland, Oreg., USA). In summary, the MelB protein was isolated and solubilized with 1.0% by weight of DDM, followed by binding the protein to a Ni$^{2+}$-NTA resin (Life Technologies, Denmark) and eluting the same with 20 mM Tris-HCl (pH 8.0), 1 mM NaCl, 199 mM KCl, 0.05% DDM, and 300 mM imidazole. Next, about 1.5 mg/ml of a protein stock was 10-fold diluted with a buffer in which DDM and imidazole are absent, but TDTs, NDTs, or DDM (control) is supplemented such that a final concentration becomes CMC+0.04% by weight or CMC+0.2% by weight. Protein samples were stored at room temperature and centrifuged at a predetermined time. To evaluate protein activity, [$^3$H]-Leu coupling was measured using scintillation proximity assay (SPA) (M. Quick et al., *Proc. Natl, Acad. Sci. U.S.A.* 2007, 104, 3603-3608). 5 μL of each protein sample dissolved in a buffer that contained 200 mM NaCl and each test compound was analyzed. SPA reaction was carried out in the presence of 20 nM [$^3$H]-Leu and copper chelate (His-Tag) YSi beads (both purchased from PerkinElmer, Denmark). [$^3$H]-Leu coupling was measured by means of a MicroBeta liquid scintillation counter (PerkinElmer).

Figure 12A:
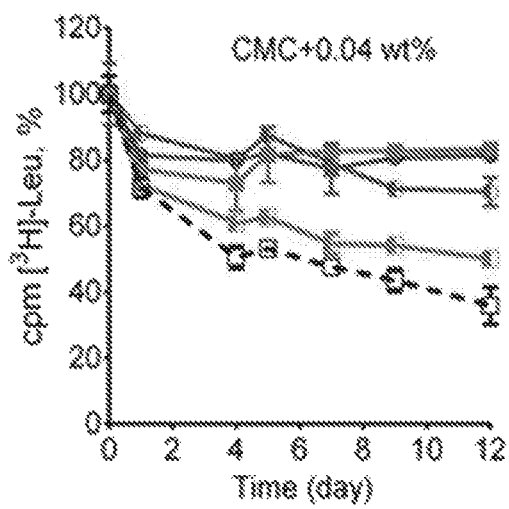
FIGS. 12a and 12b illustrate stability of LeuT proteins by TDTs or NDTs, which are used in a concentration of (a) CMC+0.04% by weight or (b) CMC+0.2% by weight, measured using scintillation proximity assay (SPA).
Figure 12:
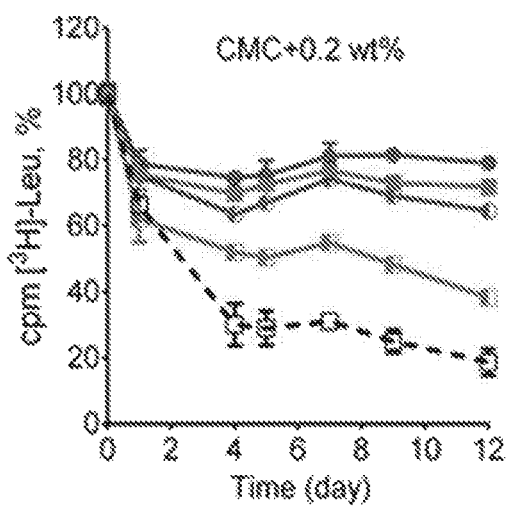

As illustrated in FIG. 12, all of the tested TDTs and NDTs exhibit LeuT protein stabilization ability superior to DDM at the two concentrations. In particular, NDT-C11 was most excellent at a concentration of CMC+0.04% by weight (FIG. 12a) and NDT-C10 and NDT-C$_{12}$ were excellent at a concentration of CMC+0.2% by weight (FIG. 12b).

<6-2> Measurement of Structural Flexibility of LeuT Protein by NDTs

In addition to the LeuT stability measurement experiments, the present inventors conducted an experiment to measure the ability of NDT-C11 to conserve structural fluidity of a transporter.

A principle of this experiment is as follows: A cysteine residue was inserted into a 192th LeuT site (E192C), followed by coupling with a thiol-reactive fluorophore (tetramethylrhodamine-5-maleimide, TMR). The prepared LeuT E192C$^{TMR}$, as TMR-coupled LeuT, is an excellent system to sensitively monitor protein structure change in response to ligand coupling. When a leucine as a biological ligand binds to an active site of LeuT, a protein exhibits structural change and, due to such structural change, TMR bonded to LeuT moves and thus the TMR is further exposed to an aqueous solution environment, whereby a hydrophobic environment is changed into a hydrophilic environment. Due to such change, TMR fluorescence molecules exposed to an aqueous solution become closer to iodide (I$^-$), as a quencher dissolved in water, whereby strong fluorescence quenching is caused. TMR quenching intensity by leucine coupling may be represented by Stern-Volmer plotting and thus structural flexibility of a protein may be directly measured. Ligand bindability of the TMR-labeled transporter was measured using SPA while increasing the amount of [$^3$H]leucine.

In particular, structure, expression, purification, and fluorescence labeling were performed according to the following methods. In accordance with a method disclosed in a paper published by C. B. Billesbølle, et al. (*J. Biol. Chem.* 2015, 290, 26725-26738), a leucine transporter mutant (LeuT E192C$^{TMR}$) was produced and purification and labeling were carried out. In summary, a residue of the E192 was mutated with cysteine using QuikChange (Agilent Technologies) such that fluorescence coupling was accomplished by maleimide labeling. The LeuT mutant was expressed in *E. coli* C41 (DE3). A membrane of DE3 was disrupted and LeuT was solubilized with 1% (w/v) DDM. Subsequently, LeuT solubilized with the amphipathic molecule was fixed to a Chelating Sepharose Fast Flow resin (GE Healthcare, Little Chalfont, UK), followed by washing with tetramethylrhodamine-5-maleimide (TMR, Life Technologies, Carlsbad, Calif., USA) at 4° C. for 16 hours. Subsequently, LeuT was eluted with a buffer containing 300 mM imidazole, 20 mM Tris-HCl (pH 8.0), 1 mM NaCl, 199 mM KCl, and 0.05% DDM.

Radioligand binding assay was carried out according to the following method. Binding was measured using scintillation proximity assay (SPA). Purified LeuT E192C$^{TMR}$ was diluted in buffer A (20 mM Tris-HCl (pH 8.0), 200 mM NaCl, 100 μM TCEP) and CMC+0.04% DDM or NDT-C11, mixed with [$^3$H]leucine (25.1 Ci mmol$^{-1}$, PerkinElmer, Waltham, Mass., USA) at determined concentrations and 0.125 mg ml$^{-1}$ YSi-Cu Histag SPA beads (PerkinElmer). Data was analyzed by non-linear regression analysis and fitted to a single-site hyperbolic function.

Fluorescence spectroscopy was carried out according to the following method. A fluorescence-based experiment was carried out by diluting 0.5 μg ml$^{-1}$ of fluorescence-labeled LeuT with buffer A supplemented with CMC+0.04% by weight of DDM, MNG-3 or NDT-C11. Leucine was separately added to specimen aliquots of LeuT for each concentration and incubated for one hour in a room temperature shaker. Steady-state fluorescence intensities were recorded with a FluoroMax4 (Horiba Scientific, Edison, N.J., USA) at λem=572 nm and excitation source at λex=552 nm at 25° C. Quencher-titration was carried out by successive additions of small specimen aliquots containing 1 M KI into buffer A supplemented with 10 mM Na$_2$S$_2$O$_3$. Fluorescence intensities (F) were corrected for sample dilution and normalized to the initial intensity (F$_0$) of a sample. All data was analyzed by linear-(Stern-Volmer plot) or nonlinear regression in GraphPad Prism 6.0 (GraphPad Software). The degree of iodide (I⁻) accessibility was obtained from the following Stern-Volmer equation: $F_0/F=1+K_{sv}\times[Q]$, where $F_0/F$ is normalized fluorescence quenching, $K_{sv}$ is a Stern-Volmer constant, and [Q] is quencher concentration. When means are calculated as a log, the means are shown as $pIC_{50}$ and the [s.e.m. interval] from $pIC_{50}\pm$s.e.m.

Values of radioligand binding constants were calculated through SPA saturation binding experiments. Values of iodide quenching-response constants and $\Delta K_{SV}$ were calculated from a site-directed fluorescence quenching spectroscopy. The affinity (Kd) is shown as means±s.e.m and $\Delta KSV$ is shown as means [s.e.m. interval]. All data is shown as means of three to four independent experiments.

Figure 13A:
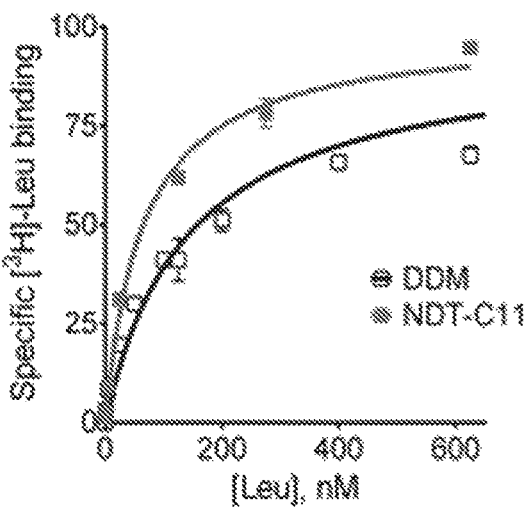
FIGS. 13a and 13b illustrates (a) [$^3$H]-leucine incorporation saturation rates (%) of protein mutants (LeuT $E192C^{TMR}$) measured by SPA when DDM or NDT-C11 is used in a concentration of CMC+0.04% by weight, and (b) Ksv values depending upon leucine concentrations when DDM, NDT-C11, or MNG-3 is used in a concentration of CMC+0.04% by weight.
Figure 13B:
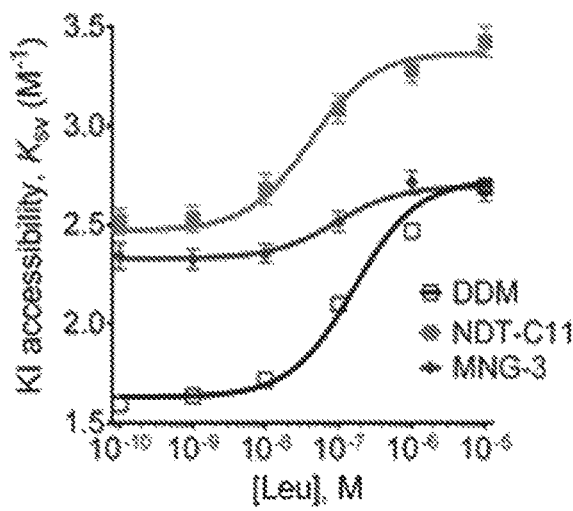
Figure 14:
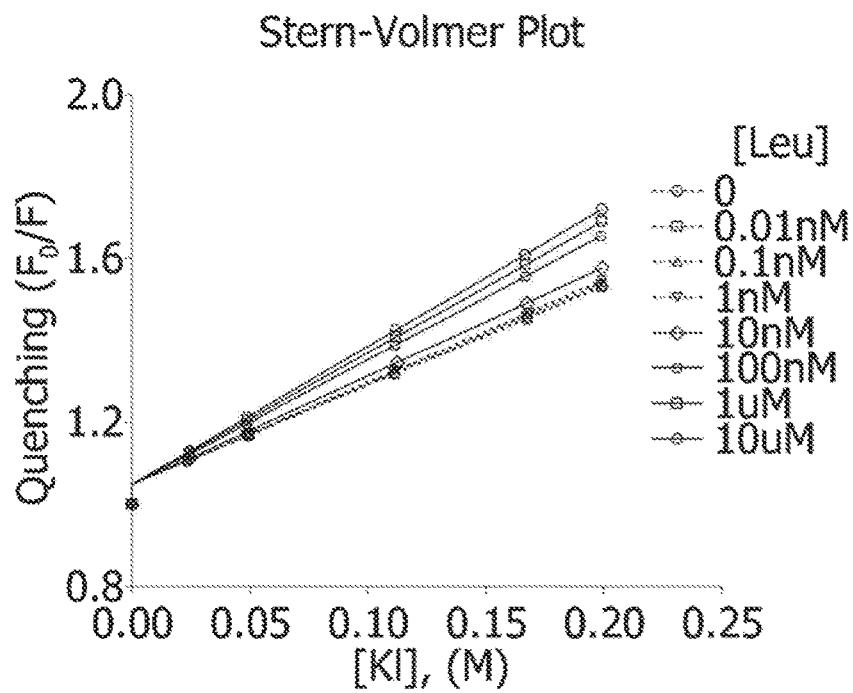
FIG. 14 illustrates fluorescence quenching ($F_0$/F) of LeuT $E192C^{TMR}$ measured at various iodide concentrations (0.00, 0.05, 0.10, 0.15, 0.20, and 0.25 M) to determine changes of accessibility in an aqueous solution of TMR fluorophores, which adhere to LeuT, dependent upon various leucine concentrations (0, 0.01 nM, 0.1 nM, 1 nM, 10 nM, 100 nM, 1 uM, 10 uM).

Ligand binding degrees of the TMR-labeled transporter were measured using SPA at increasing [³H]leucine concentrations and are illustrated in FIG. 13a. Radioligand binding constants and iodide quenching-response constants are summarized in Table 2 below. Fluorescence quenching of LeuT E192C$^{TMR}$ was measured while gradually increasing the concentration of iodide at various leucine concentrations. Results are illustrated in FIG. 14. In addition to this data, Stern-Volmer constant ($K_{sv}$) changes dependent upon leucine concentrations are shown as functions in FIG. 13b.

TABLE 2

|  | $K_d$ (nM) | $EC_{50}$ (nM) | $\Delta K_{SV}$ (M⁻¹) |
|---|---|---|---|
| DDM | 141.8 ± 18 | 163 [118; 227] | 1.1 [1.04; 1.17] |
| NDT (C11) | 64 ± 6.5 | 41 [19; 87] | 0.9 [0.78; 1.03] |
| MNG-3 | N.D.ᵃ | 94 [42; 209] | 0.37 [0.32; 0.43] |

ᵃN.D. = not determined

Results shown in FIGS. 13 and 14 and Table 2 are comprehensively reviewed. The $K_d$ value of the transporter solubilized by NDT-C11 is slightly lower than that of the protein solubilized by DDM. This indicates that binding to the leucine, as a ligand, is stronger (Table 2). As results confirmed from plot of $K_{sv}$ and [Leu], the transporter solubilized by each of DDM, NDT-C11, MNG-3 shows saturation reaction according to leucine concentrations and the $EC_{50}$ values which are respectively measured as 163 nM, 41 nM, and 94 nM (Table 2). The observed $EC_{50}$ values correspond to [³H]leucine affinity measured by SPA. Relative TMR accessibility changes ($\Delta K_{sv}$) by I⁻ may be provided as indicators of limitation degrees of protein structural changes by an amphipathic molecule micelle. The $K_{sv}$ value of NDT-C11 is 0.9 M⁻¹ and, similarly, the $K_{sv}$ value of DDM is 1.1 M⁻¹. However, the $K_{sv}$ value of MNG-3 is much smaller 0.4 M⁻¹ (Table 2). From such data, it can be assumed that NDT-C11, unlike MNG-3, satisfactorily maintains the structural fluidity of the LeuT protein similarly to DDM. In addition, interestingly, $K_{sv}$ remarkably increases with NDT-C11, compared to DDM, when leucine is absent ($K_{sv}$ increases up to 1.6 with DDM, but up to 2.5 with NDT-C11). This is believed to occur because the aqueous solution accessibility of initial TMR of the LeuT protein not binding to ligand becomes greater with NDT-C11 and thus the LeuT protein is less surrounded by the amphipathic molecules.

That is, it is anticipated that NDT-C11 occupies fewer hydrophilic portions (particularly, a loop area in a cell) of the protein and thus more portions are exposed to the outside, whereby protein crystallization is facilitated. Protein crystals tend to be satisfactorily formed with increasing hydrophilic parts of a membrane protein exposed to an aqueous solution.

From these results, it can be confirmed that NDT-C11 maintains the structural flexibility of the LeuT protein even while exhibiting an effect superior to DDM and similar to MNG-3 in stabilizing the LeuT protein, thus having superior ability as an amphipathic molecule. MNG-3 is excellent in stabilizing a membrane protein, but tends to greatly limit the structural fluidity of a protein. Therefore, NDT-C11 is anticipated to play an important role in determining a membrane protein structure and to be broadly utilized in protein function research requiring the structural fluidity of membrane proteins.

What is claimed is:

1. A compound represented by the following Formula 1:

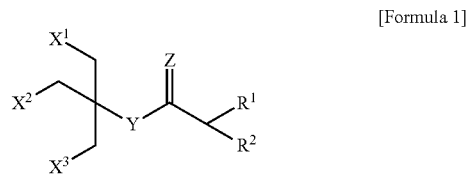

[Formula 1]

wherein R¹ and R² are each independently a substituted or unsubstituted $C_3$-$C_{20}$ alkyl group, a substituted or unsubstituted $C_3$-$C_{20}$ cycloalkyl group, or a substituted or unsubstituted $C_3$-$C_{20}$ aryl group;

X¹, X² and X³ are each independently an oxygen-linked saccharide;

Y is —CH₂O— or NH; and

Z is absent or O.

2. The compound according to claim 1, wherein the saccharide is a monosaccharide or a disaccharide.

3. The compound according to claim 1, wherein the saccharide is a glucose.

4. The compound according to claim 1, wherein R¹ and R² are a $C_7$ to $C_{14}$ alkyl group; R¹ and R² are the same; X¹ to X³ are an oxygen-linked glucose; Y is NH; and Z is O.

5. The compound according to claim 1, wherein R¹ and R² are a $C_7$ to $C_{14}$ alkyl group; R¹ and R² are the same; X¹ to X³ are an oxygen-linked glucose; Y is —CH₂O—; and Z is absent.

6. The compound according to claim 1, wherein the compound is represented by the following Formula 2, 3, 4, 5, 6, 7, 8, or 9:

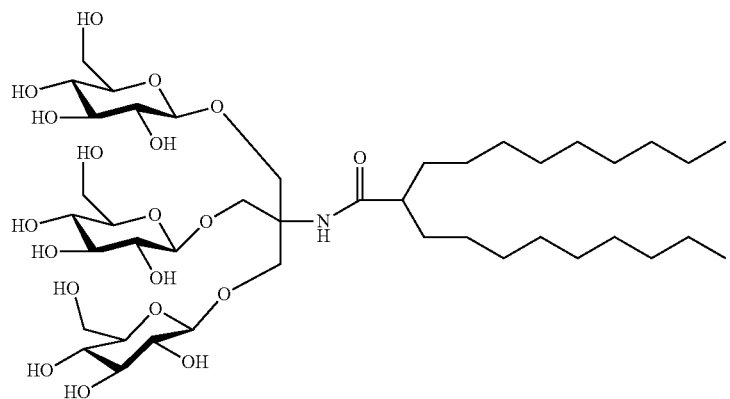
[Formula 2]
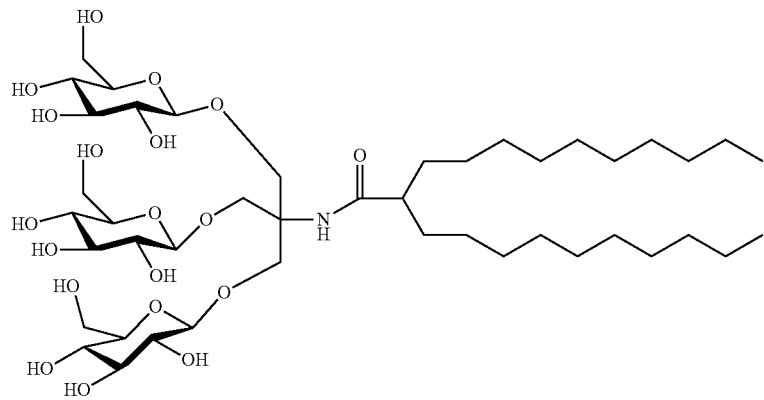
[Formula 3]
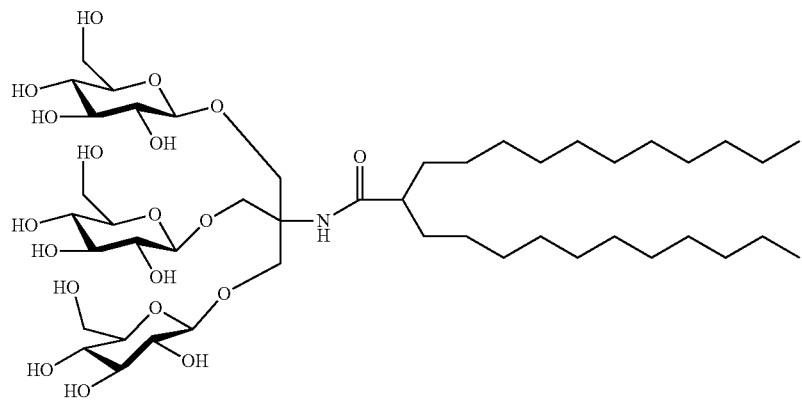
[Formula 4]
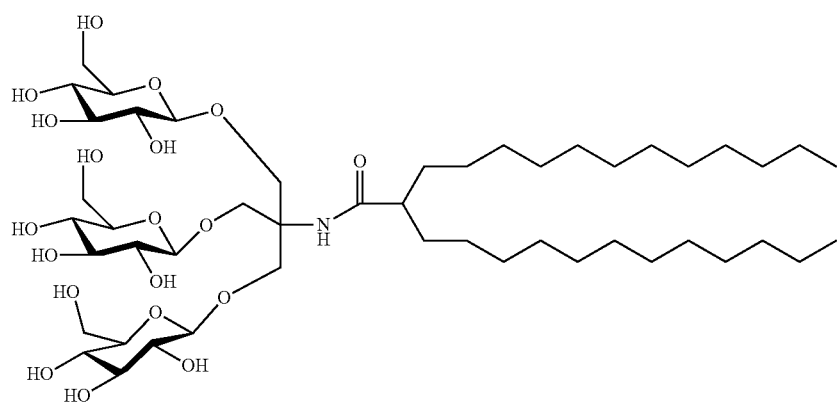
[Formula 5]

[Formula 6]
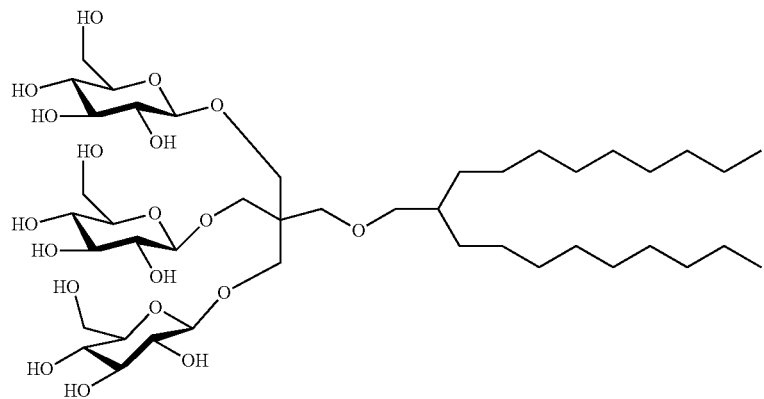
[Formula 7]
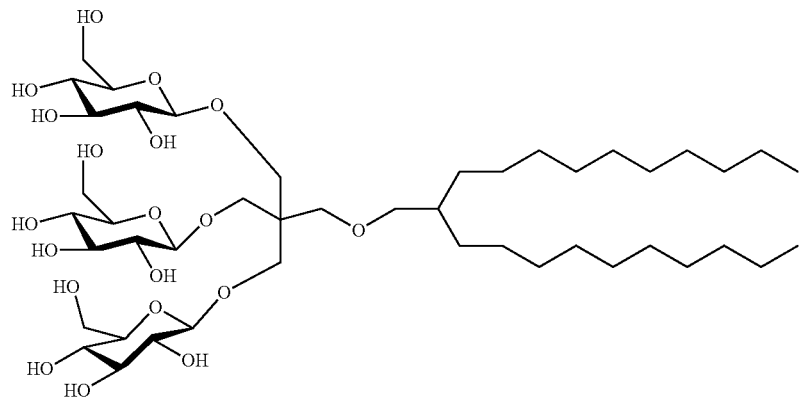
[Formula 8]
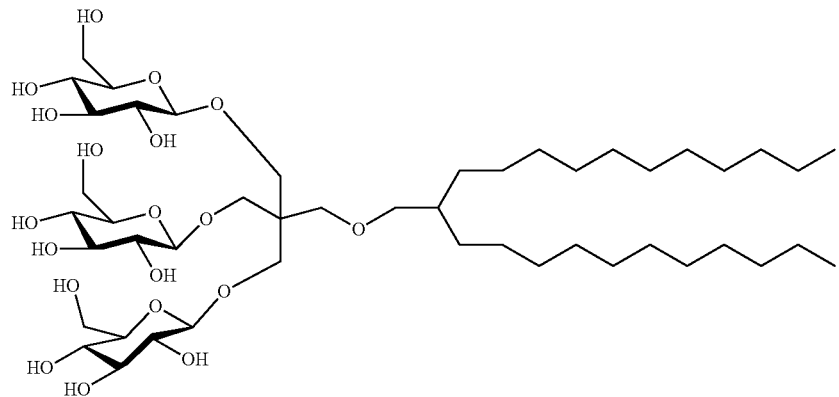
[Formula 9]
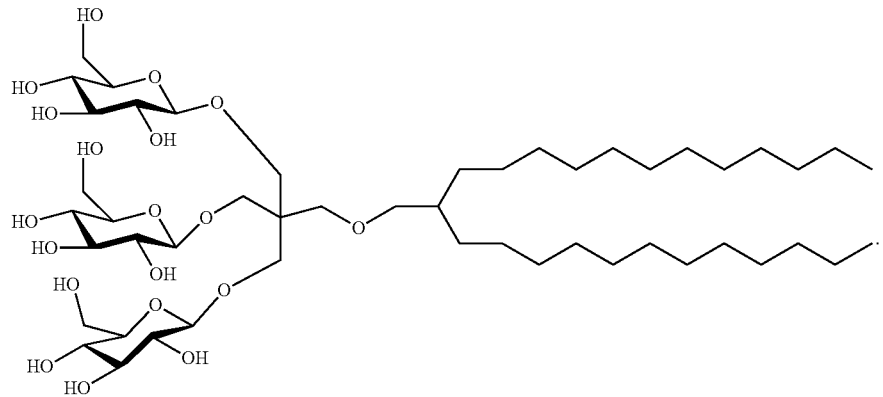

7. The compound according to claim 1, wherein the compound is an amphipathic molecule for extracting, solubilizing, stabilizing, crystallizing or analyzing a membrane protein.

8. The compound according to claim 1, wherein the compound has a critical micellar concentration (CMC) of 0.1 μM to 500 μM in an aqueous solution.

9. A composition for extracting, solubilizing, stabilizing, crystallizing or analyzing a membrane protein, the composition comprising the compound according to claim 1.

10. The composition according to claim 9, wherein the composition is a micelle, liposome, emulsion, or nanoparticle formulation.

11. A method of preparing a compound represented by the following Formula 1, the method comprising:
 1) generating dialkylated dimethylmalonate by adding alkyl iodide to dimethylmalonate;
 2) generating dialkylated monoester by allowing demethoxy carbonylation of a product generated by step 1);
 3) introducing an amide linker by adding tris(hydroxymethyl)aminomethane to a product generated by step 2);
 4) introducing a saccharide, to which a protective group is attached, by allowing glycosylation of a product generated by step 3); and
 5) removing an O-benzoyl group by allowing deprotection of a product generated by step 4):

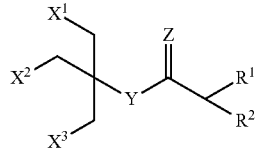

[Formula 1]

wherein $R^1$ and $R^2$ are a $C_7$ to $C_{14}$ alkyl group; $R^1$ and $R^2$ are the same; $X^1$ to $X^3$ are an oxygen-linked glucose; Y is NH; and Z is O.

12. A method of preparing a compound represented by the following Formula 1, the method comprising:
 1) generating dialkylated dimethylmalonate by adding alkyl iodide to dimethylmalonate;
 2) generating dialkylated mono-ol by allowing dialkylated ester reduction of a product generated by step 1);
 3) generating dialkylated tri-ol, into which an ether linker is introduced, by adding 4-(bromomethyl)-1-methyl-2,6,7-trioxabicyclo[2.2.2]-octane to a product generated by step 2);
 4) introducing a saccharide, to which a protective group is attached, by allowing glycosylation of a product generated by step 3); and
 5) removing an O-benzoyl group by allowing deprotection of a product generated by step 4):

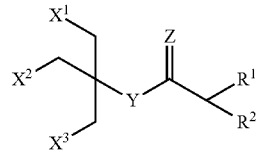

[Formula 1]

wherein $R^1$ and $R^2$ are a $C_7$ to $C_{14}$ alkyl group; $R^1$ and $R^2$ are the same; $X^1$ to $X^3$ are an oxygen-linked glucose; Y is —CH$_2$O—; and Z is absent.

13. A method of extracting, solubilizing, stabilizing, crystallizing, or analyzing a membrane protein, the method comprising treating a membrane protein in an aqueous solution with a compound represented by the following Formula 1:

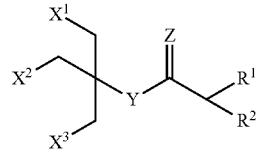

[Formula 1]

wherein $R^1$ and $R^2$ are each independently a substituted or unsubstituted $C_3$-$C_{20}$ alkyl group, a substituted or unsubstituted $C_3$-$C_{20}$ cycloalkyl group, or a substituted or unsubstituted $C_3$-$C_{20}$ aryl group;
$X^1$, $X^2$ and $X^3$ are each independently an oxygen-linked saccharide;
Y is —CH$_2$O— or NH; and
Z is absent or O.

14. The method according to claim 13, wherein $R^1$ and $R^2$ are a $C_7$ to $C_{14}$ alkyl group; $R^1$ and $R^2$ are the same; $X^1$ to $X^3$ are an oxygen-linked glucose; Y is NH; and Z is O.

15. The method according to claim 13, wherein $R^1$ and $R^2$ are a $C_7$ to $C_{14}$ alkyl group; $R^1$ and $R^2$ are the same; $X^1$ to $X^3$ are an oxygen-linked glucose; Y is —CH$_2$O—; and Z is absent.

16. The method according to claim 13, wherein the membrane protein is a uric acid-xanthine/H+ symporter (UapA), a melibiose permease (MelB), a leucine transporter (LeuT), a G-protein coupled receptor (GPCR), or a combination of two or more thereof.

* * * * *